United States Patent
Koepke et al.

(10) Patent No.: US 7,879,369 B2
(45) Date of Patent: Feb. 1, 2011

(54) COMBRETUM LAURIFOLIUM MART. EXTRACT AND METHODS OF EXTRACTING AND USING SUCH EXTRACT

(75) Inventors: Peter Koepke, Cold Spring, NY (US); Ven Subbiah, Garner, NC (US); Matthew E. Burow, Slidell, LA (US)

(73) Assignee: SelvaMedica, LLC, Wappingers Falls, NY (US)

( * ) Notice: Subject to any disclaimer, the term of this patent is extended or adjusted under 35 U.S.C. 154(b) by 0 days.

(21) Appl. No.: 12/032,984

(22) Filed: Feb. 18, 2008

(65) Prior Publication Data

US 2009/0074891 A1 Mar. 19, 2009

Related U.S. Application Data

(60) Provisional application No. 60/973,400, filed on Sep. 18, 2007.

(51) Int. Cl.
A61K 33/00 (2006.01)
(52) U.S. Cl. ..................................................... 424/725
(58) Field of Classification Search .................. None
See application file for complete search history.

(56) References Cited

U.S. PATENT DOCUMENTS

| | | | |
|---|---|---|---|
| 3,954,737 A | 5/1976 | Rinehart, Jr. et al. |
| 4,145,345 A | 3/1979 | Beemsterboer et al. |
| 4,151,042 A | 4/1979 | Higashide et al. |
| 4,241,536 A | 12/1980 | Saint-Firmin |
| 4,254,111 A | 3/1981 | Pegel et al. |
| 4,313,946 A | 2/1982 | Powell et al. |
| 4,315,929 A | 2/1982 | Freedman et al. |
| 4,328,309 A | 5/1982 | Chalmers et al. |
| 4,405,613 A | 9/1983 | Hecht |
| 4,418,064 A | 11/1983 | Powell et al. |
| 4,701,559 A | 10/1987 | Horii et al. |
| 4,940,726 A | 7/1990 | Pettit et al. |
| 5,180,676 A | 1/1993 | Ichikawa et al. |
| 5,208,020 A | 5/1993 | Chari et al. |
| 5,301,694 A | 4/1994 | Raymond et al. |
| 5,380,738 A | 1/1995 | Norman et al. |
| 5,393,790 A | 2/1995 | Reitz et al. |
| 5,409,953 A | 4/1995 | Pettit et al. |
| 5,416,064 A | 5/1995 | Chari et al. |
| 5,593,530 A | 1/1997 | Hashiguchi |
| 5,830,509 A | 11/1998 | West et al. |
| 5,962,737 A | 10/1999 | West |
| 6,124,362 A | 9/2000 | Bradbury et al. |
| 6,165,245 A | 12/2000 | Yamashita |
| 6,333,410 B1 | 12/2001 | Chari et al. |
| 6,376,557 B1 | 4/2002 | Zaveri |
| 6,383,521 B1 | 5/2002 | Shin et al. |
| 6,406,720 B1 | 6/2002 | Pauly et al. |
| 6,441,163 B1 | 8/2002 | Chari et al. |
| 6,451,777 B1 | 9/2002 | Bradbury et al. |
| 6,455,573 B1 | 9/2002 | Pinto et al. |
| 6,475,258 B1 | 11/2002 | Yamashita |
| 6,485,857 B2 | 11/2002 | Perry et al. |
| 6,544,524 B2 | 4/2003 | Heerklotz et al. |
| 6,555,120 B1 | 4/2003 | Aluja-Schuneman et al. |
| 6,648,026 B2 | 11/2003 | Look et al. |
| 6,689,744 B2 | 2/2004 | Gao et al. |
| 6,695,510 B1 | 2/2004 | Look et al. |
| 6,746,695 B1 | 6/2004 | Martin et al. |
| 6,790,954 B2 | 9/2004 | Chung et al. |
| 6,824,780 B1 | 11/2004 | Devaux et al. |
| 6,914,130 B2 | 7/2005 | Gao et al. |
| 7,074,802 B2 | 7/2006 | Doughty et al. |
| 7,108,868 B2 | 9/2006 | Jia et al. |
| 7,141,599 B2 | 11/2006 | Gregory et al. |
| 7,144,590 B2 | 12/2006 | Kuhrts |
| 2002/0041788 A1 | 4/2002 | Look et al. |
| 2002/0048589 A1 | 4/2002 | Heerklotz et al. |
| 2002/0076450 A1 | 6/2002 | Pauly et al. |
| 2003/0049296 A1 | 3/2003 | Knauf et al. |
| 2003/0072820 A1 | 4/2003 | Pauly et al. |
| 2003/0104076 A1 | 6/2003 | Berkulin et al. |
| 2003/0110527 A1 | 6/2003 | Ogawa et al. |

(Continued)

FOREIGN PATENT DOCUMENTS

WO WO2004039412 A2 5/2004

OTHER PUBLICATIONS

Kamb (Nature Reviews: Drug Discovery (2005), vol. 4, pp. 161-165).*
Suffredini (Anti-Cancer Agents in Medicinal Chemistry (2006), vol, 6, pp. 367-375).*
Mohammed et al. "Cyclooxygenase inhibitors in urinary bladder cancer: in vitro and in vivo effects". Mol Cancer Ther, vol. 6, No. 2 (Feb. 2006) 329-336.*
Idu et al. "Hypotensive Effects and Acute Toxicity Property of Methanol Extract of *Baissea axillaris* Hau. Leaf on Animal Models" Journal of Biological Sciences (2008) abstract only.*
Woon et al. "NF-kappa B activation in vivo in both host and tumour cells by the antivascular agent 5,6-dimethylxanthenone-4-acetic acid (DMXAA)". European Journal of Cancer. vol. 39, Issue 8 (May 2003) 1176-1183, abstract only.*

(Continued)

*Primary Examiner*—Amy L Clark
(74) *Attorney, Agent, or Firm*—Patton Boggs LLP

(57) ABSTRACT

A method of inhibiting COX-2, inhibiting NF-Kappa B activation, treating inflammation, or treating cancer may comprise administering a therapeutically effective amount of an extract of *Combretum laurifolium* Mart. to a patient. A medicament as described herein may comprise a pharmaceutically acceptable vehicle and a therapeutically effective amount of an extract of *Combretum laurifolium* Mart. suspended in the vehicle. A method of making an extract of *Combretum laurifolium* Mart. may comprise creating a component solution by treating *Combretum laurifolium* Mart. material with an extractor and a solvent and producing an extract by at least partially removing liquid from the component solution. An extract of *Combretum laurifolium* Mart. may comprise components extracted using various solvents.

5 Claims, 20 Drawing Sheets

U.S. PATENT DOCUMENTS

| | | |
|---|---|---|
| 2003/0165532 A1 | 9/2003 | Heerklotz et al. |
| 2003/0170292 A1 | 9/2003 | Yong et al. |
| 2003/0219799 A1 | 11/2003 | Horrigan et al. |
| 2003/0228305 A1 | 12/2003 | Frantz et al. |
| 2003/0228319 A1 | 12/2003 | Frantz et al. |
| 2003/0236303 A1 | 12/2003 | Gribble et al. |
| 2004/0001840 A1 | 1/2004 | Young et al. |
| 2004/0002091 A1 | 1/2004 | Young et al. |
| 2004/0002463 A1 | 1/2004 | Honda et al. |
| 2004/0005598 A1 | 1/2004 | DeVaux et al. |
| 2004/0007284 A1 | 1/2004 | Look et al. |
| 2004/0043446 A1 | 3/2004 | DeFrees et al. |
| 2004/0052868 A1 | 3/2004 | Asiedu et al. |
| 2004/0063911 A1 | 4/2004 | DeFrees et al. |
| 2004/0077836 A1 | 4/2004 | DeFrees et al. |
| 2004/0081681 A1 | 4/2004 | Vromen |
| 2004/0082026 A1 | 4/2004 | DeFrees et al. |
| 2004/0115168 A1 | 6/2004 | DeFrees et al. |
| 2004/0122083 A1 | 6/2004 | Petit et al. |
| 2004/0126807 A1 | 7/2004 | Goddard et al. |
| 2004/0126838 A1 | 7/2004 | DeFrees et al. |
| 2004/0132640 A1 | 7/2004 | DeFrees et al. |
| 2004/0142856 A1 | 7/2004 | DeFrees et al. |
| 2004/0146539 A1 | 7/2004 | Gupta |
| 2004/0161435 A1 | 8/2004 | Gupta |
| 2004/0161524 A1 | 8/2004 | Sakai et al. |
| 2004/0166069 A1 | 8/2004 | Gupta |
| 2004/0171554 A1 | 9/2004 | Deshayes et al. |
| 2004/0175439 A1 | 9/2004 | Cyr |
| 2004/0192579 A1 | 9/2004 | Tze et al. |
| 2004/0198969 A1 | 10/2004 | Baldwin et al. |
| 2004/0208902 A1 | 10/2004 | Gupta |
| 2004/0219124 A1 | 11/2004 | Gupta |
| 2004/0228884 A1 | 11/2004 | Gupta |
| 2004/0229232 A1 | 11/2004 | Davis et al. |
| 2004/0229277 A1 | 11/2004 | Frantz et al. |
| 2004/0235068 A1 | 11/2004 | Levinson |
| 2004/0235840 A1 | 11/2004 | Chari et al. |
| 2004/0241114 A1 | 12/2004 | Gupta |
| 2004/0241174 A1 | 12/2004 | Amphlett et al. |
| 2004/0241703 A1 | 12/2004 | DeSauvage et al. |
| 2004/0258696 A1 | 12/2004 | Frantz et al. |
| 2004/0268443 A1 | 12/2004 | Wu et al. |
| 2005/0003513 A1 | 1/2005 | Chung et al. |
| 2005/0009105 A1 | 1/2005 | Goddard et al. |
| 2005/0031584 A1 | 2/2005 | DeFrees et al. |
| 2005/0036942 A1 | 2/2005 | Devaux et al. |
| 2005/0042216 A1 | 2/2005 | Frantz et al. |
| 2005/0048008 A1 | 3/2005 | Gupta |
| 2005/0053608 A1 | 3/2005 | Weber et al. |
| 2005/0059087 A1 | 3/2005 | Weber et al. |
| 2005/0064492 A1 | 3/2005 | DeSauvage et al. |
| 2005/0065139 A1 | 3/2005 | Pinto et al. |
| 2005/0098857 A1 | 5/2005 | Shoji |
| 2005/0100982 A1 | 5/2005 | DeFrees et al. |
| 2005/0106644 A1 | 5/2005 | Cairns et al. |
| 2005/0106667 A1 | 5/2005 | Fellouse et al. |
| 2005/0107595 A1 | 5/2005 | Cairns et al. |
| 2005/0112129 A1 | 5/2005 | Phillips |
| 2005/0123925 A1 | 6/2005 | Ashkenazi et al. |
| 2005/0124012 A1 | 6/2005 | Simon et al. |
| 2005/0130949 A1 | 6/2005 | Frydman et al. |
| 2005/0144831 A1 | 7/2005 | Knauf et al. |
| 2005/0152894 A1 | 7/2005 | Krummen et al. |
| 2005/0159588 A1 | 7/2005 | Gao et al. |
| 2005/0159591 A1 | 7/2005 | Gao et al. |
| 2005/0164250 A1 | 7/2005 | Ashkenazi et al. |
| 2005/0166274 A1 | 7/2005 | French et al. |
| 2005/0169858 A1 | 8/2005 | Look et al. |
| 2005/0169933 A1 | 8/2005 | Steeves et al. |
| 2005/0170368 A1 | 8/2005 | Ashkenazi et al. |
| 2005/0176046 A1 | 8/2005 | Ashkenazi et al. |
| 2005/0176825 A1 | 8/2005 | Pero |
| 2005/0202559 A1 | 9/2005 | Pownall et al. |
| 2005/0209310 A1 | 9/2005 | Chaplin et al. |
| 2005/0271608 A1 | 12/2005 | Gupta |
| 2005/0272824 A1 | 12/2005 | Pinney et al. |
| 2006/0074108 A1 | 4/2006 | Gupta |
| 2006/0122181 A1 | 6/2006 | Ikemoto et al. |
| 2006/0228426 A1 | 10/2006 | Cyr |
| 2006/0246162 A1 | 11/2006 | Cleveland et al. |
| 2007/0154575 A1 | 7/2007 | Shimoda et al. |

OTHER PUBLICATIONS

Suh, et al., "A Novel Synthetic Oleanane Triterpenoid, 2-Cyano-3,12-dioxoolean-1,9-dien-28-oic Acid, with Potent Differentiating, Antiproliferative, and Anti-Inflammatory Activity", Cancer Research 59, pp. 336-341, Jan. 15, 1999 (6 pages).

Nishino, et al., "Inhibition of the Tumor-promoting Action of 12-O-Tetradecanoylphorbol-13-acetate by Some Oleanane-type Triterpenoid Compounds", Cancer Research 48, pp. 5210-5215, Sep. 15, 1988 (6 pages).

Zhang, et al., "The Novel Synthetic Oleanane Triterpenoid CDDO (2-cyano-3, 12-dioxoolean-1, 9-dien-28-oic acid) Induces Apoptosis in Mycosis Fungoides/Sézary Syndrome Cells", The Society of Investigative Dermatology, Inc. (Aug. 2004) (8 pages).

Kutney, et al., "Anti-inflammatory oleanane triterpenes from *Tripterygium wilfordii* cell suspension cultures by fungal elicitation", Plant Cell Reports (1993) 12:356-359 (4 pages).

Huguet, et al., "Effect of triterpenoids on the inflammation induced by protein kinase C activators, neuronally acting irritants and other agents", European Journal of Pharmacology 410 (2000) pp. 69-81 (13 pages).

Park, et al., "Chemical Enhancers of Cytokine Signaling that Suppress Microfilament Turnover and Tumor Cell Growth", Cancer Research 2006; 66: (7). Apr. 1, 2006 (9 pages).

Ukiya, et al., "Anti-Inflammatory, Anti-Tumor-Promoting, and Cytotoxic Activities of Constituents of Marigold (*Calendula officinalist*) Flowers", Journal of National Products 2006, 69, pp. 1692-1696 (5 pages).

Banno, et al., "Anti-inflammatory and Antitumor-Promoting Effects of the Triterpene Acids from the Leaves of *Eriobotrya japonica*", Biol. Pharm. Bull. 28(10) 1995-1999 (2005) (5 pages).

Brookes, et al., "The Triterpenoid 2-Cyano-3, 12-dioxooleans-1,9-dien-28-oic Acid and Its Derivatives Elicit Human Lymphoid Cell Apoptosis through a Novel Pathway Involving the Unregulated Mitochondrial Permeability Transition Pore", Cancer Research 2007; 67: (4). Feb. 15, 2007 (10 pages).

Honda, et al., "Partial Synthesis of Krukovines A and B, Triterpene Ketones Isolated from the Brazilian Medicinal Plant *Maytenus krukovii*", Journal of National Products 1997, 60, pp. 1174-1177 (4 pages).

Vedantam, "Doctors Warned About Common Drugs for Pain; NSAIDs Tied to Risk of Heart", The Washington Post—Washington, D. C., Feb. 27, 2007, A.8, A Section (1 page).

Fernandez, et al., "Seasonal changes in photosynthesis of trees in the flooded forest of the Mapire River", Tree Physiology 19, pp. 79-85; Oct. 9, 1997 (7 pages).

Sanchez, et al., "Use of chigo (*Campsiandra comosa* Benth) seeds in human nutrition. III. Energetic value of chiga flour", Arch Latinoam Nutr. Sep. 1987;37(3):454-67 (1 page), abstract only.

Barreiro, et al., "Use of chigo seed (*Campsiandra comosa*, Benth) in human nutrition. II. Process of non-industrial manufacture of chiga", Arch Latinoam Nutr. Sep. 1984;34(3):531-42 (1 page), abstract only.

Barreiro, et al., "Use of chigo seed (*Campsiandra comosa*, Benth) in human nutrition. I. Antecedents, nutritional potential, and characteristics of the plan and seed", Arch Latinoam Nutr. Sep. 1984;34(3):523-30 (1 page), abstract only.

Adedeji, et al., "Free and Glycosidically Bound Aroma Compounds in Hog Plum (*Spondias mombins* L.)", J. Agric. Food Chem. 1991, 39, pp. 1494-1497 (4 pages).

Allegrone, et al., "Identification of Volatile Components of Caja Fruit (*Spondias lutea* L.) and Chiral Analysis of 3-Hydroxy Aliphatic Esters", Flavor and Fragrance Journal vol. 7, pp. 337-342 (May 28, 1992) (6 pages).

Bailey, "Manual of Cultivated Plants Most commonly grown in the continental United States and Canada", The MacMillan Company, New York 1949 (2 pages).

Corthout, et al., "Antiviral Ellagitannins From *Spondias mombin*", Phytochemistry, vol. 30, No. 4, pp. 1129 1130, 1991 (2 pages).

Corthout, et al., "Antiviral Caffeoyl Esters From *Spondias mombin*", Phytochemistry, vol. 31, No. 6, pp. 1979-1981, 1992 (3 pages).

Dalziel, et al., "The Useful Plants of West Tropical Africa", The Crown Agents for the Colonies, 4, Millbank, Westminister, London, S.W.1 1948 (3 pages).

Gamble, "A Manual of Indian Timbers an Account of the Growth, Distributions, and Uses of the Trees and Shrubs of India and Ceylon with Descriptions of Their Wood-Structure", London Sampson Low, Marston & Company 1922 (3 pages).

Hedrick, "Sturtevant's Notes on Edible Plants", State of New York—Department of Agriculture Twenty-seventh Annual Report—vol. 2—Part II, 1919 (3 pages).

Hill, "Economic Botany A Textbook of Useful Plants and Plant Products", Second Edition McGraw-Hill Book Company, Inc. 1952 (2 pages).

Hooker, "The Flora of British India", vol. II. Sabiacea to Cornacea, L. Reeve & Co., Ltd. 1879 (2 pages).

Howes, "Vegetable Tanning Materials", London Butterworths Scientific Publications 1953 (2 pages).

Irvine, "Woody Plants of Ghana With Special Reference to Their Uses", London Oxford University Press 1961 (3 pages).

Kanjilal, et al., "Flora of Assam", Government of Assam, Shillong. vol. I, pp. 341-342, 1940 (2 pages).

Mudaliar, et al., "Advances in Agricultural Sciences and their Applications", The Role of Green Manuring in Soil Management; Coimbatore. pp. 227-228, 1965 (2 pages).

Mabberley, "The Plant-Book A Portable Dictionary of the Vascular Plants", Second Edition, Cambridge University Press 1997 (3 pages).

Sundararaj, et al., "Guide to the Economic Plants of South India", Periodical Expert Book Agency D-42, Vivek Vihar, Delhi (no date) (2 pages).

"The Silviculture of Indian Trees", vol. I, Dilleniaceae to Leguminosae (Papilionaceae) Yale Forestry Library (no date) (5 pages).

Winton, et al., "The Structure and Composition of Foods", vol. II Vegetables, Legumes, Fruits, John Wiley & Sons, Inc., London: Chapman & Hall, Limited 1935 (3 pages).

Coates, et al., "A Novel β-Lactamase Inhibitor Isolated From *Spondias mombin*", Journal of National Products, vol. 57, No. 5, pp. 654-657, May 1994 (4 pages).

Hamano, et al., "Composition of Carotenoids from Commercial Products of Caja (*Spondias lutea*)", Journal of Food Composition and Analysis (2001) 14, pp. 335-343 (9 pages).

Franco, et al., "Volatile Composition of Some Brazilian Fruits: Umbu-caja (*Spondias citherea*), Camu-camu (*Myrciaria dubia*), Araca-boi (*Eugenia stipitata*), and Cupuacu (*Theobroma grandiflorum*)", J. Argic. Food Chem. 2000 48, pp. 1263-1265 (3 pages).

Rodrigues, et al., "Antimicrobial activities of secondary metabolites produced by endophytic fungi from *Spondias mombin*", J. Basic Microbiol. 40 (2000) 4, pp. 261-267 (7 pages).

Abo, et al., "Antimicrobial Potential of *Spondias mombin, Croton zambesicus* and *Zygotritonia crocea*", Phytotherapy Research 13, pp. 494-497 (1999) (4 pages).

Jirovetz, et al., "Analysis of the aroma compounds of the fruit extracts of *Spondias cytherea* ("ambarella") from Cameroon", Z Lebensm Unters Forsch A (1999) 208:74-76 (3 pages).

Wang, et al., "Inhibitory Activity of Unsaturated Fatty Acids and Anacardic Acids toward Soluble Tissue Factor—Factor VIIa Complex", J. Nat. Prod. 1998, 61, pp. 1352-1355 (4 pages).

Villegas, et al., "Evaluation of the wound-healing activity of selected traditional medicinal plants from Perú", Journal of Ethnopharmacology 55 (1997) pp. 193-200 (8 pages).

Mackeen, et al., "Antinematodal Activity of Some Malaysian Plant Extracts against the Pine Wood Nematode, *Bursaphelenchus xylophilus*", Pestic. Sci. 1997, 51, pp. 165-170 (6 pages).

Mohamed, et al., "Antimycotic Screening of 58 Malaysian Plants against Plant Pathogens", Pestic. Sci. 1996, 47, pp. 259-264 (6 pages).

Corthout, et al., "Antibacterial and Molluscicidal Phenolic Acids from *Spondias mombin*", Planta Med. 60 (1994) pp. 460-463 (4 pages).

Cáceres, et al., "Plants used in Guatemala for the treatment of gastrointestinal disorders. 3. Confirmation of activity against enterobacteria of 16 plants", Journal of Ethnopharmacology, 38 (1993) pp. 31-38 (8 pages).

Caceres, et al., "Plants Used in Guatemala for the Treatment of Gastrointestinal Disorders. 1. Screening of 84 Plants Against Enterobacteria", Journal of Ethnopharmacology, 30 (1990) pp. 55-73 (19 pages).

Corthout, et al., "Isolation and Characterization of Geraniin Gallcyl-Geraiin from *Spondias mombin*", Planta Med. 56 (1990) (2 pages).

Corthout, et al., "The Long-Chain Phenolic Acids of *Spondias mombin*", Planta Med. 56 (1990) (1 page).

Offiah, et al., "Abortifacient Activity of an Aqueous Extract of *Spondias mombin* Leaves", Journal of Ethnopharmacology, 26 (1989) pp. 317-320 (4 pages).

Angeh, et al., "Antimicrobial and anti-inflammatory activity of four known and one new triterpenoid from *Combretum imberbe* (combretaceae)", Journal of Ethnopharmacology, vol. 110, pp. 55-60, 2007 (5 pages).

Cirla, et al., "Combretastatins: from natural products to drug discovery", Natural Products Reports, vol. 20, pp. 558-564, 2003 (7 pages).

Dark, et al., "Combretastatin A-4, an Agent That Displays Potent and Selective Toxicity toward Tumor Vasculature", Cancer Research, vol. 57, pp. 1829-1834, May 15, 1997 (6 pages).

Eldeen. et al. "Antibacterial, anti-inflammatory, anti-cholinesterase and mutagenic effects of extracts obtained from some trees used in South African traditional medicine" Journal of Ethnopharmacology, vol. 102, pp. 457-464, 2005 (8 pages).

McGaw. et al., "An investigation on the biological activity of *Combretum* species" Journal of Ethnopharmacology, vol. 75, pp. 45-50, 2001 (6 pages).

Murata. et al., "Interaction between combretastatin A-4 disodium phosphate and radiation in murine tumors" Radiotherapy and Oncology, vol. 60, pp. 155-161, 2001 (7 pages).

Olumayokun. et al., "Evaluation of the anti-inflammatory property of the extract of *Combretum micranthum* G. Don (Combretaceae)" Inflammopharmacology, vol. 11 (3), pp. 293-298, 2003 (6 pages).

Petit. et al., "Antineoplastic Agents. 291. Isolation and Synthesis of Combretastatins A-4, A-5, and A-6" J. Med. Chem., vol. 38, pp. 1666-1672, 1995 (7 pages).

Petit. et al., "Isolation, Structure, Synthesis, and Antimitotic Properties of Combretastatins B-3 and B-4 from *Combretum caffrum*" Journal of Natural Products, vol. 51 (3), pp. 517-527, 1988 (11 pages).

Petit. et al., "Isolation, Structure, and Synthesis of Combretastatins A-1 and B-1, Potent New Inhibitors of Microtubule Assembly, Derived from *Combretum caffrum*" Journal of Natural Products, vol. 50 (1) pp. 119-131, 1987 (13 pages).

Li. et al., "Conformationally restricted analogs of Combretastatin A-4 derived from SU 5416" Bioorganic & Medicinal Chemistry Letters, vol. 15, pp. 5382-5385, 2005 (4 pages).

Schwikkard et al., "Bioactive Compounds from *Combretum erythrophyllum*" Journal of Natural Products, vol. 63, pp. 457-460, 2000 (4 pages).

Tozer et al., "The biology of the combretastatins as tumour vascular targeting agents" International Journal of Experimental Pathology, vol. 83, pp. 21-38, 2002 (18 pages).

Xia et al., "Antitumor Agents. 181. Synthesis and Biological Evaluation of 6,7,2',3',4'-Substituted-1,2,3,4-tetrahydro-2-phenyl-4-quinolines as a New Class of Antimitotic Antitumor Agents" Journal of Medicinal Chemistry, vol. 41, pp. 1155-1162, 1998 (8 pages).

PCTUS0868032, WO, Oct. 7, 2008, SelvaMedica, LLC, International Search Report.

PCTUS0869424, WO, Sep. 26, 2008, SelvaMedica, LLC, International Search Report.

PCTUS0868035, WO, Sep. 11, 2008, SelvaMedica, LLC, International Search Report.
PCTUS0871816, WO, Oct. 24, 2008, SelvaMedica, LLC, International Search Report.
PCTUS0871626, WO, Oct. 20, 2008, SelvaMedica, LLC, International Search Report.
Bera, et al., "A Novel Azeotropic Mixture of Solvent Extraction of Edible Oils", Agricultural Engineering International, CIGR Ejournal, Manuscript FP 06 005, vol. VIII, Apr. 2006 (6 pages).
Thring, et al., "Antimicrobial activities of four plant species from Southern Overberg region of South Africa", African Journal of Biotechnology, Vo. 6 (15), pp. 1779-1784, Aug. 6, 2007 (6 pages).
Yoshikawa, et al., "Hepatoprotective and Antioxidative Properties of *Salacia reticulata*: Preventive Effects of Phenolic Constituents on CCl4-Induced Liver Injury in Mice", Biol. Pharm. Bull. 25(1) 72-76, Jan. 2002 (5 pages).
Bremner, et al., "Natural products as targeted modulators of the nuclear factor-κB pathway", Journal of Pharmacy and Pharmacology, vol. 54, pp. 453-472, 2002 (20 pages).
www.rain-tree.com/campsiandra.htm, Tropical Plant Database, Huacupurana (*Campsiandra angustifolia*), website accessed Oct. 8, 2008 (5 pages).
Abad, et al., "Antiinflammatory activity of some medicinal plant extracts from Venezuela", Journal of Ethnopharmacology, 55, 63-68, Aug. 24, 1996 (6 pages).
Kim, et al., "Cytotoxic Anticancer Candidates from Natural Resources", Curr. Med. Chem.—Anti-Cancer Agents, vol. 2, No. 4, p. 485-537, 2002 (53 pages).
www.rain-tree.com/ubos.htm, Tropical Plant Database, Ubos (*Spondias mombin*), website accessed Oct. 13, 2008 (9 pages).
Pannangpetch, et al., "The ethanolic extract of *Combretum decandrum* Roxb. improved glucose tolerance and increased glucose uptake of hyperinsulinemic rats", European Congress of Endocrinology, European Society of Endocrinology, 2006 (1 page).
Suffredini, et al., "In vitro, cytotoxic activity of Brazilian plant extracts against human lung, colon and CNS solid cancers and leukemia", Elserier B.V., pp. 223-226, Feb. 6, 2007, (4 pages), Fitoterapia.
Pettit, et al., "Antineoplastic Agents, 122. Constitutents of *Combretum caffrum*", Journal of Natural Products, vol. 50, No. 3, pp. 386-391, May-Jun. 1987 (6 pages).
www.tradeavail.com/combretum.html. "*Combretum caffrum*", Trade Avail Bio Research & Discovery, webpage accessed Jun. 5, 2009 (2 pages).
Honda, et al., "Partial Synthesis of Krukovines A and B, Triterpene Ketones Isolated from the Brazilian Medicinal Plant *Maytenus krukovii*", J. Nat. Prod. 1997, 60, pp. 1174-1177 (4 pages).
Shirota, et al., "Triterpenes from Brazilian Medicinal Plant "Chuchuhuasi" (*Maytenus krukovii*)", J. Nat. Prod. 1996, 59, pp. 1072-1075 (4 pages).
Duarte, et al., "Stem and leaf morphoanatomy of *Maytenus ilicifolia*", Fitoterapia 76 (2005) pp. 41-49 (9 pages).
Nakagawa, et al., "Chemical Constituents from the Colombian medicinal Plant *Maytenus laevis*", J. Nat. Prod. 2004, 67, pp. 1919-1924 (6 pages).
Ferreira, et al., "A lyophilized aqueous extract of *Maytenus ilicifolia* leaves inhibits histamine-mediated acid secretion in isolated frog gastric mucosa", Planta (2004) 219: pp. 319-324 (6 pages).
Cipriani, et al., "An Arabinogalactan Isolated from the Medicinal Plant *Maytenus ilicifolia*", J. Nat. Prod. 2004, 67, pp. 703-706 (4 pages).
Mossi, et al., "Extraction and characterization of volatile compounds in *Maytenus ilicifolia*, using high-pressure CO2" Fitoterapia 75 (2004) pp. 168-178 (11 pages).
Núñez, et al., "Insecticidal Sesquiterpene Pyridine Alkaloids from *Maytenus chiapensis*", J. Nat. Prod. 2004, 67, pp. 14-18 (5 pages).
Ohsaki, et al., "Four New Triterpenoids from *Maytenus ilicifolia*", J. Nat. Prod. 2004, 67, pp. 469-471 (3 pages).
Shirota, et al., "Two Cangorosin a Type Triterpene Dimers from *Maytenus chuchuhuasca*", Chem. Pharm. Bull. 52 (9) pp. 1148-1150 (2004) (3 pages).

Corsino, et al., "Antioxidant Flavan-3-ols and Flavonol Glycosides from *Maytenus aquifolium*", Phytotherapy Research 17, pp. 913-916 (2003) (4 pages).
Matu, et al., "Antibacterial and anti-inflammatory activities of some plants used for medicinal purposes in Kenya", Journal of Ethnopharmacology 87 (2003) pp. 35-41 (7 pages).
Tabach, et al., "Evaluation of the anti-ulcerogenic activity of a dry extract of *Maytenus ilicifolia* Martius ex. Reiss produced by a jet spouted bed dryer", Pharmazie 58: pp. 573-576 (2003) (4 pages).
Núñez, et al., "Absolute Configuration and Complete Assignment of 13C NMR Data for New Sesquiterpenes from *Maytenus chiapensis*", J. Nat. Prod. 2003, 66, pp. 572-574 (3 pages).
Coelho, et al., "Chemical Constituents from the Infusion of *Zollernia ilicifolia* Vog. and Comparison with *Maytenus* Species", Journal of Zeitschrift für Naturforschung C, vol. No. 1/2, pp. 47-52 (Jan./Feb. 2003) (7 pages).
Hnatyszyn, et al., "Argentinian plant extracts with relaxant effect on the smooth muscle of the corpus cavernosum of Guinea pig", Phytomedicine 10: pp. 669-674, 2003 (6 pages).
Horn, et al., "Antimutagenic activity of extracts of natural substances in the Salmonella/microsome assay", Mutagenesis vol. 18 No. 2 pp. 113-118, 2003 (6 pages).
Montanari, et al., "Effect of *Maytenus ilicifolia* Mart. on pregnant mice", Contraception 65 (2002) pp. 171-175 (5 pages).
Filho, et al., "Quantitative Determination of Cytotoxic Friedo-nor-oleanane Derivatives from Five Morphological Types of *Maytenus ilicifolia* (Celastraceae) by Reverse-phase High-performance Liquid Chromatography", Phytochemical Analysis 13, pp. 75-78 (2002) (4 pages).
Pullen, et al., "New and bioactive compounds from *Streptomyces* strains residing in the wood of Celastraceae", Planta (2002) 216: pp. 162-167 (6 pages).
Vilegas, et al., "Application of On-line C30 RP-HPLC-NMR for the Analysis of Flavonoids from Leaf Extract of *Maytenus aquifolium*", Phytochemical Analysis 11, pp. 317-321 (2000) (5 pages).
González, et al., "Anti-Tumor Promoting Effects of Sesquiterpenes from *Maytenus cuzcoina* (Celastraceae)", Bioorgantic & Medical Chemistry 8 (2000) pp. 1773-1778 (6 pages).
Piacente, et al., "Laevisines A and B: Two New Sesquiterpene—Pyridine Alkaloids from *Maytenus laevis*", J. Nat. Prod. 1999, 62, pp. 161-163 (3 pages).
Hussein, et al., "Phenolics from *Maytenus senegalensis*", Phytochemistry 50 (1999) pp. 689-694 (6 pages).
Vilegas, et al., "Isolation and Structure Elucidation of Two New Flavonoid Glycosides from the Infusion of *Maytenus aquifolium* Leaves. Evaluation of the Antiulcer Activity of the Infusion", J. Agric. Food Chem. (1999) 47, pp. 403-406 (4 pages).
González, et al., "Triterpene Trimers from *Maytenus scutioides*: Cycloaddition Compounds?" J. Nat. Prod. (1999) 62, pp. 1185-1187 (3 pages).
Tahir, et al., "Antiplasmodial activity of selected Sudanese medicinal plants with emphasis on *Maytenus senegalensis* (Lam.) Exell.", Journal of Ethnopharmacology 64 (1999) pp. 227-233 (7 pages).
Pérez-Victoria, et al., "New Natural Sesquiterpenes as Modulators of Daunomycin Resistance in a Multidrug-Resistant *Leishmania tropica* Line", J. Med. Chem. (1999), 42, pp. 4388-4393 (6 pages).
Chávez, et al., "New Phenolic and Quinone—Methide Triterpenes from *Maytenus amazonica*", J. Nat. Prod. (1999), 62, pp. 434-436 (3 pages).
Alvarenga, et al., "A New Antibiotic Nortriterpene Quinone Methide from *Maytenus catingarum*", J. Nat. Prod. (1999), 62, pp. 750-751 (2 pages).
Larson, et al., "Two New Maytansinoids from *Maytenus buchananii*", J. Nat. Prod. (1999), 62, pp. 361-363 (3 pages).
Vilegas, et al., "Isolation and Structure Elucidation of Two New Flavonoid Glycosides from the Infusion of *Maytenus aquifolium* Leaves. Evaluation of the Antiulcer Activity of the Infusion", J. Agric. Food Chem. (1999), 47, pp. 403-406 (4 pages).
Chavez, et al., "Sesquiterpene Polyol Esters from the Leaves of *Maytenus macrocarpa*", J. Nat. Prod. (1999), 62, pp. 1576-1577 (2 pages).
Chen, et al., "Design, synthesis, and biological evaluation of N-acetyl-2-carboxybenzenesulfonamides: a novel class of cyclooxygenase-2 (COX-2) inhibitors", Bioorganic & Medicinal Chemistry 13 (2005) pp. 2459-2468 (10 pages).

Liu, et al., "A New Class of Glucosidase Inhibitor: Analogues of the Naturally Occurring Glucosidase Inhibitor Salacinol with Different Ring Heteroatom Substituents and Acyclic Chain Extension", J. Org. Chem. (2006), 71, pp. 3007-3013 (7 pages).

Yoshikawa, et al., "Absolute Stereostructure of Potent Glucosidase Inhibitor, Salacinol, with Unique Thiosugar Sulfonium Sulfate Inner Salt Structure from *Salacia reticulata*", Bioorganic & Medicinal Chemistry 10 (2002) pp. 1547-1554 (8 pages).

Chen, et al., "Synthesis, enzymatic activity, and X-ray crystallography of an unusual class of amino acids", Bioorganic & Medicinal Chemistry 14 (2006) pp. 8332-8340 (9 pages).

Kumar, et al., "Synthesis of D-lyxitol and D-ribitol analogues of the naturally occurring glycosidase inhibitor salacinol", Carbohydrate Research 340 (2005) pp. 2612-2619 (8 pages).

Morikawa, et al,. "Structures of New Friedelane-Type Triterpenes and Eudesmane-Type Sesquiterpene and Aldose Reductase Inhibitors from *Salacia chinensis*", J. Nat. Prod. (2003), 66, pp. 1191-1196 (6 pages).

http://www.bionatus.com/nutramedix/pages/cumanda_what.htm, "What is Cumanda?", webpage accessed on Dec. 8, 2008 (1 page).

http://www.pestdepot.addr.com/chuchu.htm, "A Real Breakthrough; New Formula", webpage accessed on Dec. 8, 2008 (7 pages).

http://www.cyberlipid.org/extract/extr0010.htm. "Automatic Soxhlet Extraction", webpage accessed May 16, 2007 (3 pages).

Raintree Nutrition, Inc., Chuchuhuasi Extract, 2 ounces, Apr. 4, 2004 (2 pages).

Wikipedia, nttp://en.wikipedia, org/wiki/Soxhlet_extractor, Soxhlet extractor, webpage accessed May 16, 2007 (2 pages).

Wikimedia Commons, http://commons, wikimedia, org/wiki/Image:Soxhlet_extractor.pmg, "Image:Soxhlet extractor.png", webpage accessed May 16, 2007 (4 pages).

www.rain-tree.com/chuchuhuasi.htm, "Chuchuhuasi", apparently first posted Dec. 19, 1996 (7 pages).

www.rain-tree.com/chuchuprod.htm. "Chuchuhuasi *Maytenus krukovii*", apparently first posted on Nov. 27, 2001 (2 pages).

\* cited by examiner

COMBRETUM LAURIFOLIUM MART. EXTRACT AND METHODS OF EXTRACTING AND USING SUCH EXTRACT

CROSS REFERENCE TO RELATED APPLICATIONS

This application claims priority to U.S. Provisional Application No. 60/973,400, filed on Sep. 18, 2007, the disclosure of which is incorporated herein by reference.

FIELD

This application relates generally to plant extracts for treating inflammation and cancer.

BACKGROUND

Rheumatoid arthritis is a chronic inflammatory disease affecting multiple tissues, but typically producing its most pronounced symptoms in the joints. It is progressive, degenerative and ultimately debilitating. The chronic inflammation in joints leads to the destruction of the soft tissue, the synovium and cartilage, as well as erosion of the articular surfaces of bones. The disease is estimated to affect over 3.2 million people in the United States, Europe and Japan. It is more prevalent in women, who are estimated to account for a majority of the cases.

Inflammation is a natural defense of the body to protect against foreign substances or injury, but it can cause problems in certain diseases. Inappropriate inflammation can be treated with traditional steroids, like the glucocorticoid cortisol, therapeutic proteins produced by recombinant DNA technology, and/or non-steroidal anti-inflammatory drugs (NSAIDs).

Prostaglandins are a family of chemicals that are produced by the cells of the body and serve many essential functions including the promotion of pain, inflammation, and fever. Additionally, some prostaglandins support the function of platelets, necessary for blood clotting, and protect the stomach lining from the damaging effects of acid. Prostaglandins are produced within the body's cells by the enzyme cyclooxygenase-2 (COX-2).

COX-2 is an enzyme involved in many functions, including but not limited to inducing pain. COX-2 is located specifically in areas of the body that are responsible for inflammation and not in the stomach. COX-2 is active in our bodies, ideally on a limited basis; however, factors such as diet, stress and injury can increase COX-2 activity. When COX-2 is active on a continual basis, constant pain ensues.

Even though the specific mechanism of action is not completely understood, it has been found that inhibiting COX-2 results in the apoptosis of cancer cells. See Johnsen, et al., "Cyclooxygenase-2 Is Expressed in Neuroblastoma, and Nonsteroidal Anti-Inflammatory Drugs Induce Apoptosis and Inhibit Tumor Growth In Vivo," Cancer Research; Vol. 64, pages 7210-7215 (Oct. 15, 2004); and Lau, et al., "Cyclooxygenase inhibitors modulate the p53/hdm2 pathway and enhance chemotherapy-induced apoptosis in neuroblastoma," Oncogene, Vol. 26, pages 1920-1931 (2007).

Therefore, plant extracts that may inhibit COX-2 may treat various diseases, including but not limited to inflammation, arthritis, muscle pain, and cancer.

SUMMARY

A method of inhibiting COX-2, inhibiting NF-Kappa B activation, treating inflammation, or treating cancer may comprise administering a therapeutically effective amount of an extract of *Combretum laurifolium* Mart. to a patient. A medicament as described herein may comprise a pharmaceutically acceptable vehicle and a therapeutically effective amount of an extract of *Combretum laurifolium* Mart. suspended in the vehicle. A method of making an extract of *Combretum laurifolium* Mart. may comprise creating a component solution by treating *Combretum laurifolium* Mart. material with an extractor and a solvent and producing an extract by at least partially removing liquid from the component solution. An extract of *Combretum laurifolium* Mart. may comprise components extracted using various solvents.

DETAILED DESCRIPTION

Figure 1:
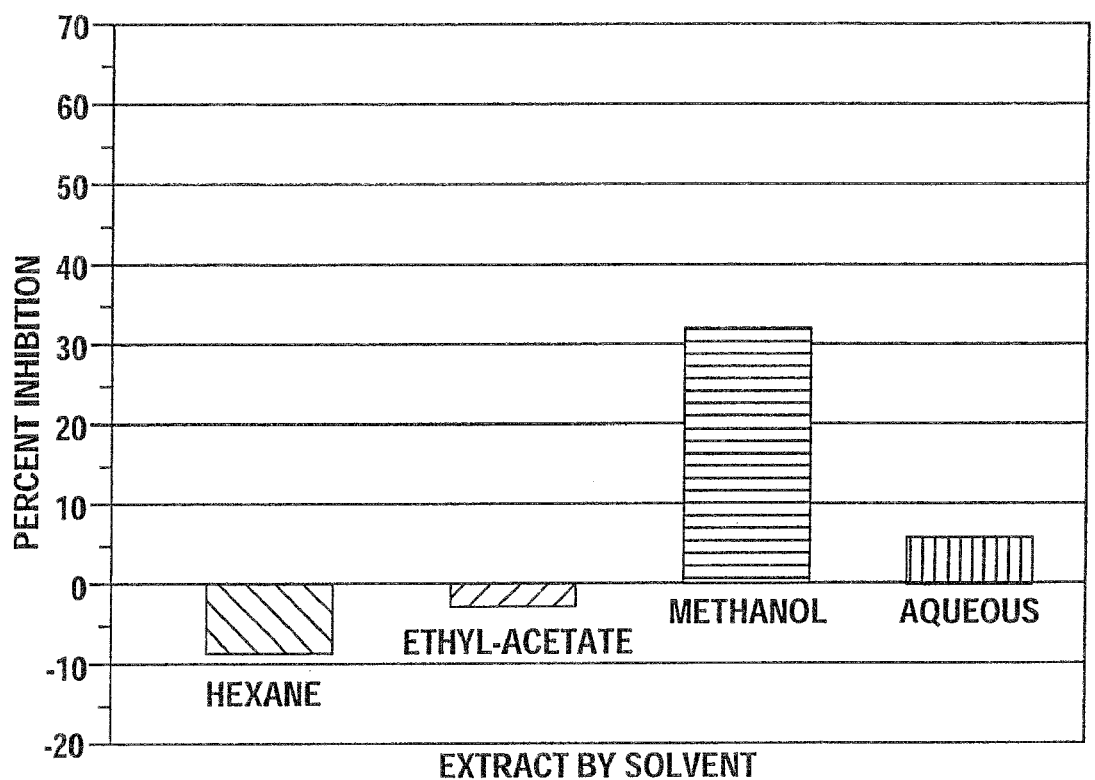
FIG. 1 is a graph that illustrates the results from an experiment to test the inhibition of COX-2 in vitro by an extract of *Combretum laurifolium* Mart. at a concentration of 9 µg/ml, extracted using four different solvents. The graph in FIG. 1 comprises percentage inhibition of human recombinant COX-2 on the y-axis, and the solvent used to extract components from the material of *Combretum laurifolium* Mart. on the x-axis.
Figure 2:
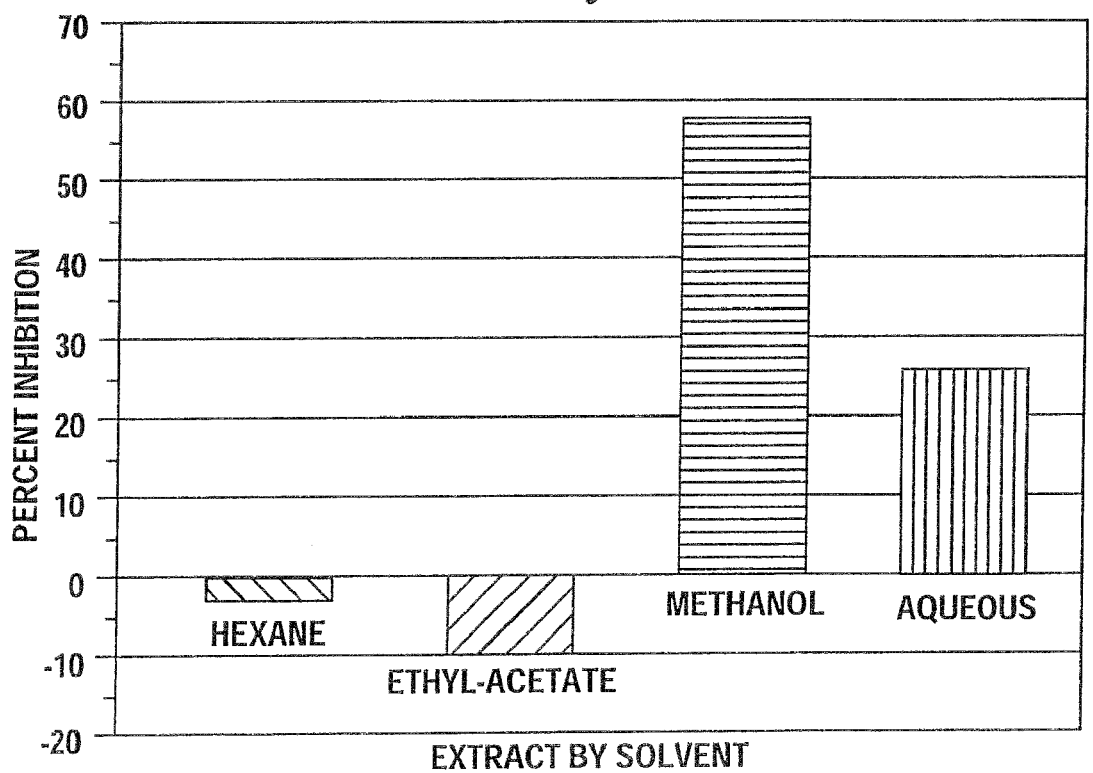
FIG. 2 is a graph that illustrates results from a replicate of the experiment of FIG. 1. The graph in FIG. 2 comprises percentage inhibition of human recombinant COX-2 on the y-axis, and the solvent used to extract components from the material of *Combretum laurifolium* Mart. on the x-axis.
Figure 3:
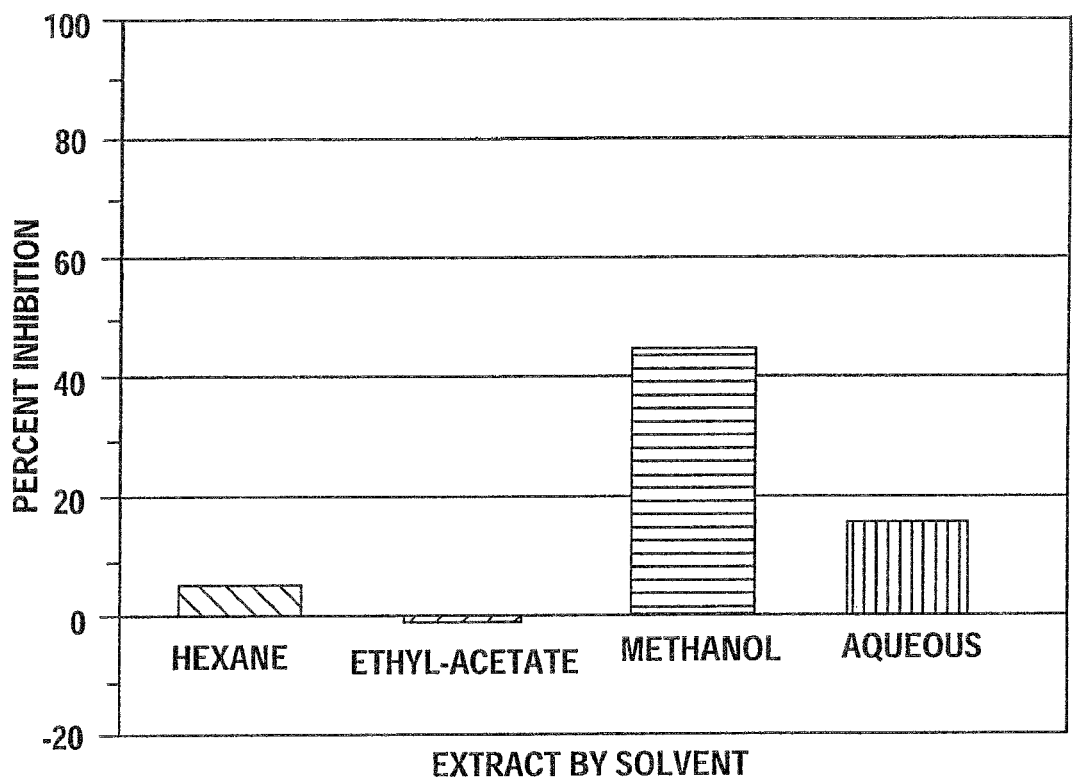
FIG. 3 is a graph that illustrates results from another replicate of the experiment of FIG. 1. The graph in FIG. 3 comprises percentage inhibition of human recombinant COX-2 on the y-axis, and the solvent used to extract components from the material of *Combretum laurifolium* Mart. on the x-axis.
Figure 4:
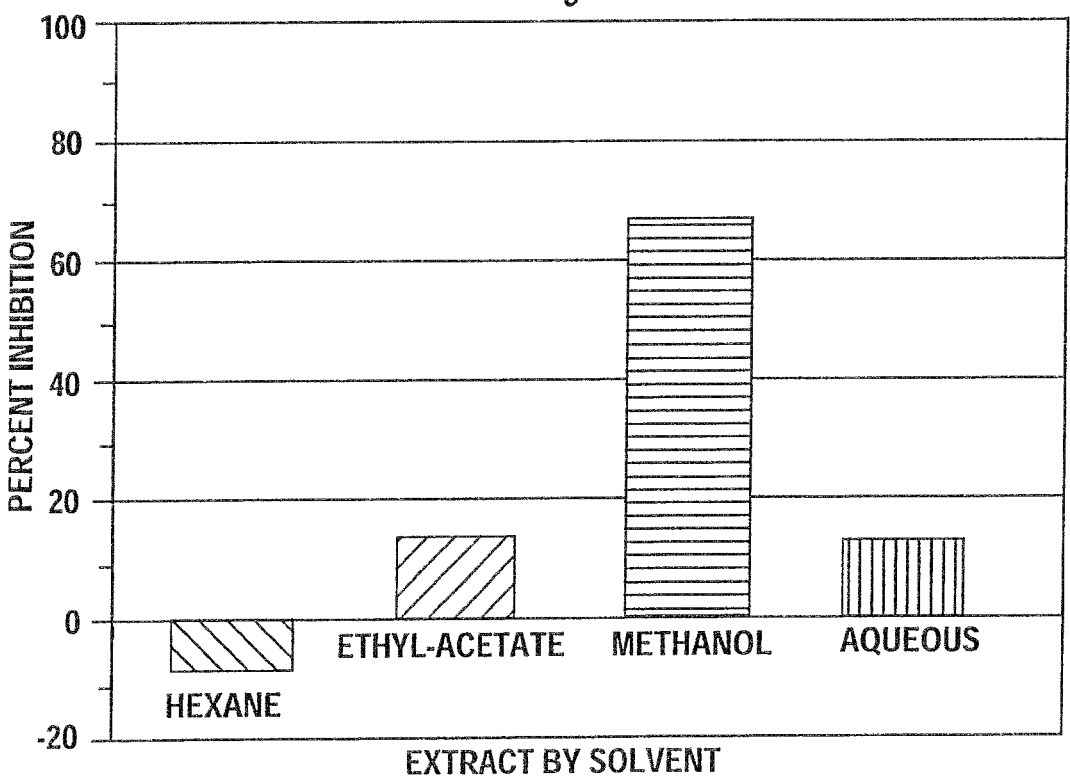
FIG. 4 is a graph that illustrates the results from yet another replicate of the experiment of FIG. 1. The graph in FIG. 4 comprises percentage inhibition of human recombinant COX-2 on the y-axis, and the solvent used to extract components from the material of *Combretum laurifolium* Mart. on the x-axis.

As used herein, the following terms should be understood to have the indicated meanings:

When an item is introduced by "a" or "an," it should be understood to mean one or more of that item.

"Component" means any gas, liquid or solid of a molecule, chemical, macromolecule, compound, or element, alone or in combination.

"Component solution" means a mixture of one or more components contained, suspended, held, or dispersed in a liquid, solid, or gas.

"Comprises" means includes but is not limited to.

"Comprising" means including but not limited to.

"Condition" means a particular state of health, such as but not limited to a disordered or incorrectly functioning organ, part, structure or system of the body, an illness, a sickness, an ailment, a disease, a physical or mental suffering, a physical or mental distress, a physical or mental sensation, a physical or mental torment, or a physical or mental pain. A condition may include cancer or inflammation.

"COX-2" means cyclooxygenase-2.

"Extractor" means an apparatus, machine, instrument, tool, or combination thereof having at least one flask adaptable to contain a solvent or solution, at least one chamber adaptable to contain a material, and at least one condenser in fluid communication with a chamber and a flask. An extractor may have a funnel adaptable to recover the solvent at some point during the extraction process. A thimble may be used in connection with an extractor. A filter may be used in connection with an extractor. An extractor may be adaptable to be subjected to heat while not decreasing the integrity of the extractor. An extractor includes, but is not limited to, a Soxhlet extractor, as invented by Franz von Soxhlet in or around 1879, and several commercially available extractors such as, but not limited to, a Soxtherm™ extractor from Gerhardt GmbH, and Soxtec Systems™, which are automated or semi-automatic extractors made by FOSS.

"Grind" means to reduce or lessen into relatively smaller particles or pieces by pulverizing, pounding, cutting, crushing, grating, rubbing harshly, carving, sawing, trimming, or dissolving an object, or a combination thereof.

"Having" means including but not limited to.

"IC50" means, with respect to a compound or formulation, the concentration of the compound or formulation that produces a 50% inhibition of COX-2.

"Inhibit" means to at least partially decrease the activity of an enzyme.

"Material" means any part of a plant including, but not limited to, bark, stem, leaf, bud, stalk, root, flower, pollen, branch, shoot, fruit, slip, vegetable, seed, or a combination thereof.

"Parenteral" means a type of route of administration of a component to a patient wherein the desired effect is systemic. Parenteral includes, but is not limited to, administering a component to a patient by injection or infusion, where such injection or infusion is intravenous, intraarterial, intramuscular, intracardiac, subcutaneous, intraosseous, intradermal, intraperitoneal, transdermal, transmucosal, inhalational, or a combination thereof.

"Patient" means a human or any other mammal.

"Pharmaceutically acceptable vehicle" means a carrier, diluent, adjuvant, or excipient, or a combination thereof, with which a component is administered to a patient. A pharmaceutically acceptable vehicle may include, but is not limited to, polyethylene glycol; wax; lactose; glucose; sucrose; magnesium stearate; silicic derivatives; calcium sulfate; dicalcium phosphate; starch; cellulose derivatives; gelatin; natural and synthetic gums such as, but not limited to, sodium alginate, polyethylene glycol and wax; suitable oil; saline; sugar solution such as, but not limited to, aqueous dextrose or aqueous glucose; DMSO; glycols such as, but not limited to, polyethylene or polypropylene glycol; lubricants such as, but not limited to, sodium oleate, sodium acetate, sodium stearate, sodium chloride, sodium benzoate, talc, and magnesium stearate; disintegrating agents, including calcium carbonate, sodium bicarbonate, agar, starch, and xanthan gum; and absorptive carriers such as, but not limited to, bentonite and klonin.

"Solvent" means a liquid or gas that has the ability to suspend, take out, draw out, separate, or attract one or more components to form a solution.

"Therapeutically effective amount" means the amount of a component that is sufficient to at least partially effect a treatment of a condition when administered to a patient. The therapeutically effective amount will vary depending on the condition, the route of administration of the component, and the age, weight, etc. of the patient being treated.

"Treat" means, with respect to a condition, to at least partially reduce, relieve, or alleviate any symptoms of the condition, to delay the onset of the condition or symptoms of the condition, to at least partially cure any symptom of the condition, or to at least partially prevent or inhibit the condition or a symptom of the condition, or a combination thereof, even if not discernible by the patient.

*Combretum laurifolium* Mart. is a plant in the family Combretaceae that typically grows in Amazonia, including but not limited to in Brazil, Peru, Columbia, Venezuela, Ecuador, Bolivia, Guyana, Suriname and French Guiana. An extract of *Combretum laurifolium* Mart. that inhibits COX-2 may be made using the methods described herein. The extraction methods involve the use of solvents to extract components of *Combretum laurifolium* Mart. that at least partially inhibit COX-2. An extract as described herein may be used to treat inflammation in a patient. Alternatively, an extract as described herein may be used to treat cancer in a patient. It is well understood by persons of ordinary skill in the art that inhibiting COX-2 decreases inflammation and contributes to the apoptosis or a decrease in the proliferation of cancer cells in humans.

An extract of *Combretum laurifolium* Mart. may be made as follows. Material from *Combretum laurifolium* Mart. may be obtained, dried and ground. Alternatively, material from *Combretum laurifolium* Mart. may be ground into small pieces and then dried. The material may be dried in an oven such as but not limited to a drying oven, at about 45 degrees Celsius, or at a temperature in the range of 46-65 degrees Celsius, to remove most of the traces of liquid from the material. The dried material may be stored at about −20 degrees Celsius, or at approximately 4 degrees Celsius or at −70 to −80 degrees Celsius, before the next steps in the extraction process. Alternatively, the next steps in the extraction process may immediately commence. Of course, other suitable drying temperatures may be used.

Either before or after drying, the material from *Combretum laurifolium* Mart. may be ground to produce smaller particle sizes. In order to obtain approximately 20-50 micron particle size, the material from *Combretum laurifolium* Mart. may be ground using a suitable grinder or pulverizer, such as a Wiley mill rotary pulverizer, for example. In addition, filters may be used to separate out and obtain approximately 20-50 micron particle size. Thereafter and between the steps in the extraction process, the material from *Combretum laurifolium* Mart. may be stored at −20 degrees Celsius, or at approximately 4 degrees Celsius or at −70 to −80 degrees Celsius or other suitable temperatures, in substantially air tight plastic bags or other containers.

About 10-100 grams of material from *Combretum laurifolium* Mart. may be subjected to extraction using an extractor. Solvents of varying polarity may be used in connection with an extractor to extract and separate the various components from the material from *Combretum laurifolium* Mart., based on the polarity or solubility of the components. Initially, material from *Combretum laurifolium* Mart. may be placed inside a "thimble" made from filter paper. The thimble may be made of any suitable permeable material. The thimble with the material from *Combretum laurifolium* Mart. may be loaded into an extractor. The extractor may have a flask containing a solvent and a condenser. The solvent may be heated, which would cause the solvent to evaporate. The hot solvent vapor travels up to the condenser, where it cools and drips down into the chamber and onto the material from *Combretum laurifolium* Mart. Within the extractor, a chamber containing material from *Combretum laurifolium* Mart. slowly fills with warm solvent. At that point, components from the material are extracted from the material and form a component solution with the solvent. When the chamber is almost full, the component solution is emptied by siphon action, back down into the flask. During each cycle, components from the material from *Combretum laurifolium* Mart. are extracted into the solvent, resulting in a component solution. This cycle may be repeated many times with each solvent. During this extraction process, clean warm solvent may be used to extract components from the material from *Combretum laurifolium* Mart. in the thimble.

With respect to the solvents that may be used in connection with the extractor, a non-polar solvent such as Hexane-1 ("hexane") or other non-polar solvents such as, but not limited to, Pentane, Cyclohexane, Heptane, Trichloroethylene, Carbon Tetrachloride, Diisopropyl Ether, or Toluene may be used. A moderately polar solvent such as Ethyl acetate-2 ("ethyl-acetate") or other moderately polar solvents such as, but not limited to, Xylene, Methyl Butyl Ether, Diethyl Ether, Dichloromethane, Dichloroethane, n-Butanol, Isopropanol, Tetrahydrofuran, Butyl Acetate, Chloroform, n-Propanol, or Methyl Ethyl Ketone may be used. A polar solvent such as Methanol-3 ("methanol") or other polar solvents such as, but not limited to, Acetone, Ethanol, Acetonitrile, Acetic Acid, Dimethyl Formamide, or Dimethyl Sulfoxide (DMSO) may be used. Extraction with the non-polar, moderately polar, and polar solvents may be performed at 45 degrees Celsius or other suitable temperatures, including but not limited to from approximately 26 degrees Celsius to approximately 60 degrees Celsius. Relatively pure water ("aqueous solvent") may be used to extract components by soaking for approximately 12 hours, or between approximately 4 hours and 12 hours or other suitable times, the material from *Combretum laurifolium* Mart. which is remaining after using any of the polar, moderately polar, or non-polar solvents and filtering out the solid material, resulting in a component solution. Alternatively, material from *Combretum laurifolium* Mart. may be soaked in relatively pure water at any point during the extraction method or independent from treating the material with any solvent. As a control, periodically samples may be drawn and analyzed to evaluate the effect of exposure time on extraction.

Following the above process, the solvent which contains various components of *Combretum laurifolium* Mart., a component solution, is located in the flask of the extractor. Liquid may be at least partially removed by drying the component solution using a rotary evaporator or other suitable evaporator including, but not limited to, a vacuum drier, a vacuum oven, nitrogen gas, a thermofuel concentrator, a centrifuge and spray drier, or other suitable drying processes. This drying process may remove substantially all of the liquid from the component solution. The resulting extract may be frozen or freeze-dried. The extract may be stored in the form of an at least partially dry powder. The extract may be transferred to scintillation vials, which may be pre-weighed, and stored at −20 degrees Celsius or at approximately 4 degrees Celsius in a refrigerator or at −70 to −80 degrees Celsius or other suitable temperatures.

The result of the above described method, if hexane, ethyl-acetate, methanol and water are used, is four extracts of *Combretum laurifolium* Mart., with each extract containing components extracted by the solvent used. These extracts will be referred to as a hexane extract, an ethyl-acetate extract, a methanol extract and an aqueous extract (collectively, the "four extracts").

Experimental Results

Experimental results demonstrate that an extract of *Combretum laurifolium* Mart. may be used to inhibit COX-2. Results described herein demonstrate that an extract of *Combretum laurifolium* Mart. inhibits NF-Kappa B activation. Results described herein also demonstrate that an extract of *Combretum laurifolium* Mart. decreases the proliferation of SK-Mel 28 cells, a human melanoma cell line and decreases cell colony count in human breast cancer cell lines. In addition, an extract of *Combretum laurifolium* Mart. results in decreased growth in tumor volume in nude mice having tumors resulting from MCF-7 and MDA-MB-231 human breast cancer cells.

COX-2 Inhibition and an Extract of *Combretum laurifolium* Mart.

An experiment that identified whether the extract of *Combretum laurifolium* Mart. at least partially inhibited COX-2 assayed peroxidase activity of human recombinant COX-2 (the "COX-2 Inhibition Assay"). The COX-2 Inhibition Assay was performed on each of the four extracts.

The COX-2 Inhibition Assay was maintained and performed at approximately 37 degrees Celsius, by use of a water bath. Briefly, human recombinant COX-2 in reaction buffer (0.1M Tris-HCl (pH 8.0), containing 5 mM EDTA and 2 mM phenol), heme, and arachidonic acid was incubated with each of the four extracts for two (2) minutes. The appearance of oxidized tetramethyl-p-phenyldiamine indicated the presence of peroxidase activity colorimetrically.

In preparation of the COX-2 Inhibition Assay, dried extracts were dissolved in methanol, Dimethyl sulfoxide ("DMSO"), or ethanol, and then diluted into the reaction buffer. The final concentration of the extracts was 9 μg/ml. 1M hydrochloric acid was added to stop COX-2 activity after a two (2) minute incubation. DUP-697, a known COX-2 inhibitor, was used as an internal control and, as expected, inhibited COX-2 with an IC50 of approximately 200 nM. The percentage inhibition of COX-2 was calculated by subtracting the quantified COX-2 activity of reactions with the extract from the quantified COX-2 activity of reactions without any COX-2 inhibitor and dividing the result by the quantified COX-2 activity of reaction without the extract. The percentage inhibition of COX-2 by the extracts ranged from 5% to 67%. The results demonstrated that the methanol extract may be more effective at inhibiting COX-2 than the ethyl-acetate extract, the hexane extract and the aqueous extract at this concentration. It is possible that an ethyl-acetate extract, a hexane extract or an aqueous extract may be more effective at inhibiting COX-2 at different concentrations. The COX-2 Inhibition Assay was conducted at least 4 times with the same variables. The results of the COX-2 Inhibition Assays described above are shown in FIGS. 1-4. Relative inhibition of COX-2 may involve the generation of an IC50 value.

Figure 5:
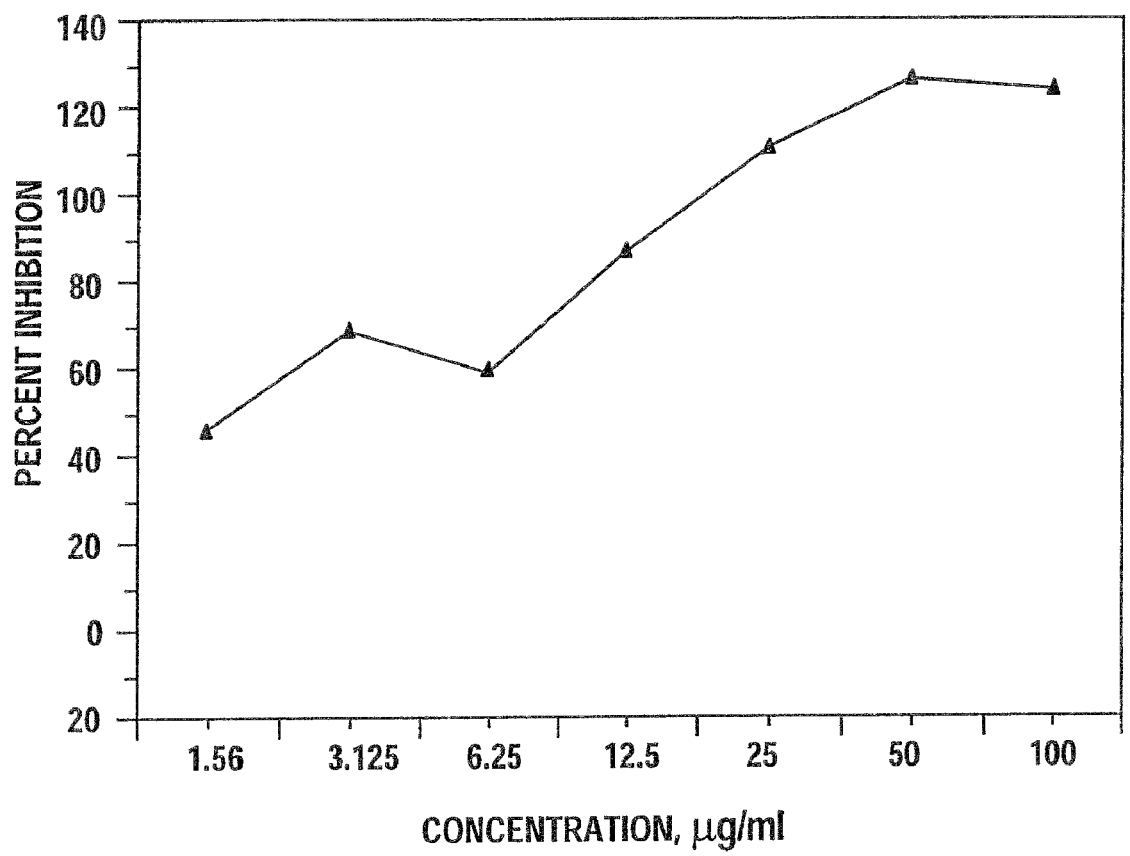
FIG. 5 is a graph that illustrates the results from an experiment to test the inhibition of COX-2 in vitro by a methanol extract of *Combretum laurifolium* Mart. at varying concentrations. The graph in FIG. 5 comprises percentage inhibition of human recombinant COX-2 on the y-axis, and concentration of the methanol extract of *Combretum laurifolium* Mart. on the x-axis.
Figure 6:
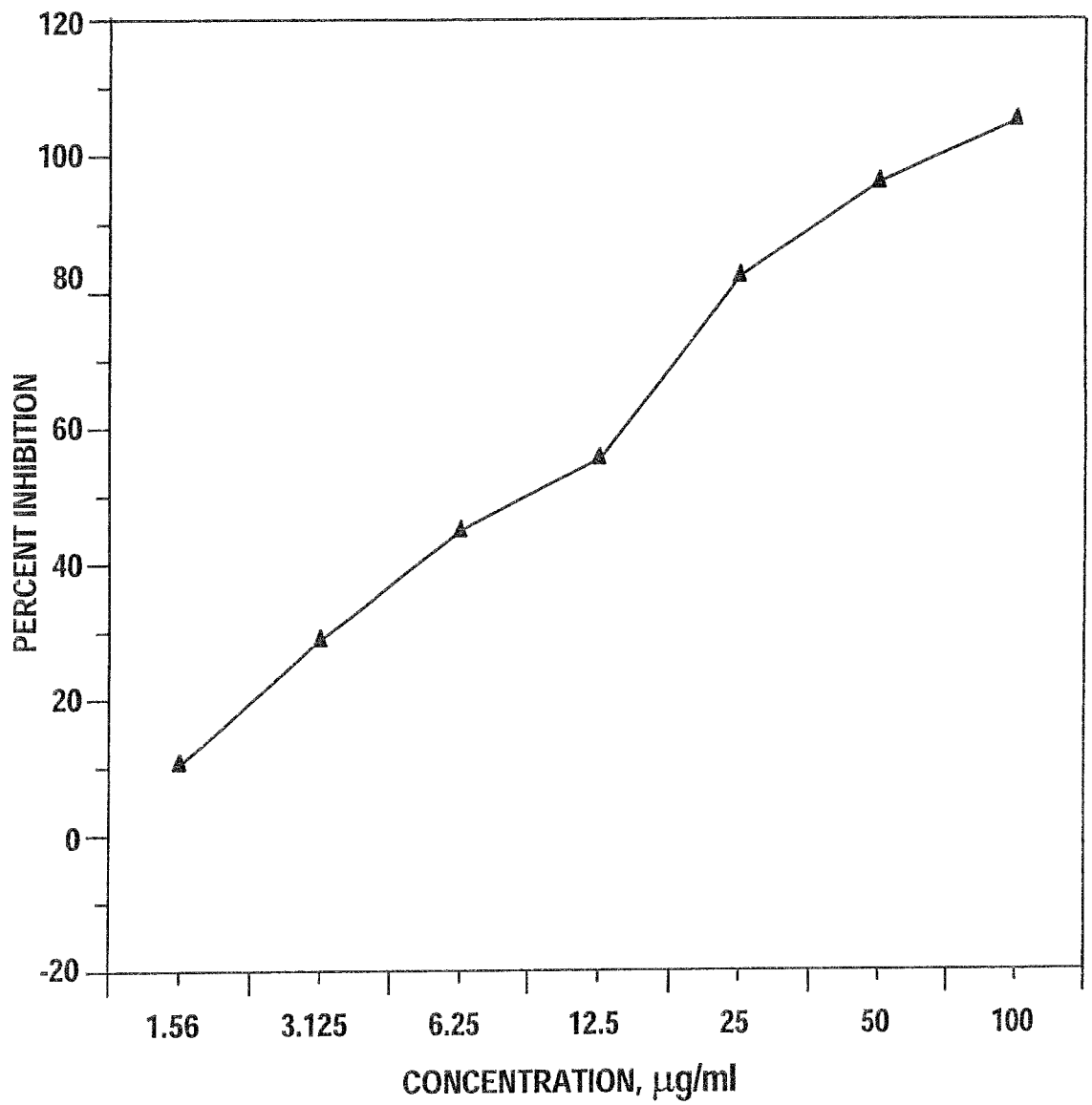
FIG. 6 is a graph that illustrates results from a replicate of the experiment of FIG. 5. The graph in FIG. 6 comprises percentage inhibition of human recombinant COX-2 on the y-axis, and concentration of a methanol extract of *Combretum laurifolium* Mart. on the x-axis.

Additionally, the methanol extract was used in a COX-2 Inhibition Assay at different concentrations ranging from 1.56 μg/ml to 100 μg/ml. The results from two identical experiments are depicted on FIG. 5 and FIG. 6. The methanol extract showed an IC50 of 2.2 μg/ml in FIG. 5 and 7.9 μ/ml in FIG. 6. A greater inhibition of COX-2 may be correlated with a higher concentration of the methanol extract.

Figure 7:
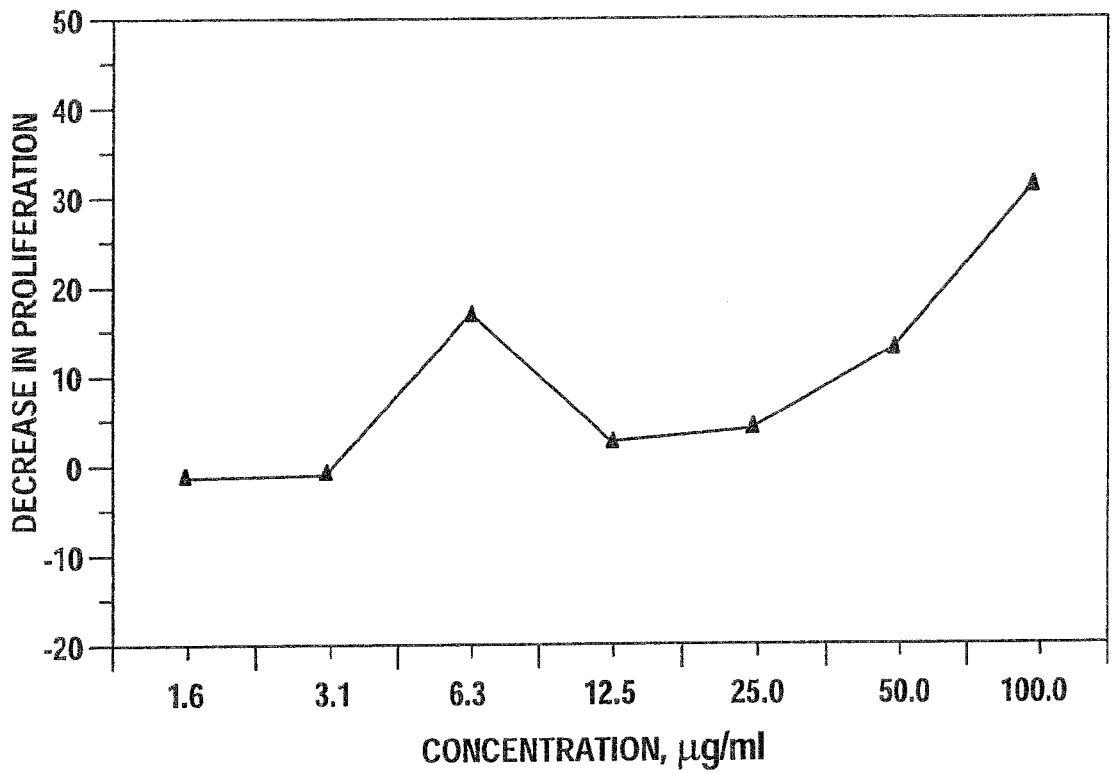
FIG. 7 is a graph that illustrates the results of an experiment to test the decrease in cell proliferation of SK-Mel 28 human melanoma cells, cultured in media with serum, caused by a methanol extract of *Combretum laurifolium* Mart. at varying concentrations. The graph in FIG. 7 comprises percentage decrease in cell proliferation on the y-axis, and concentration of a methanol extract of *Combretum laurifolium* Mart. on the x-axis.
Figure 8:
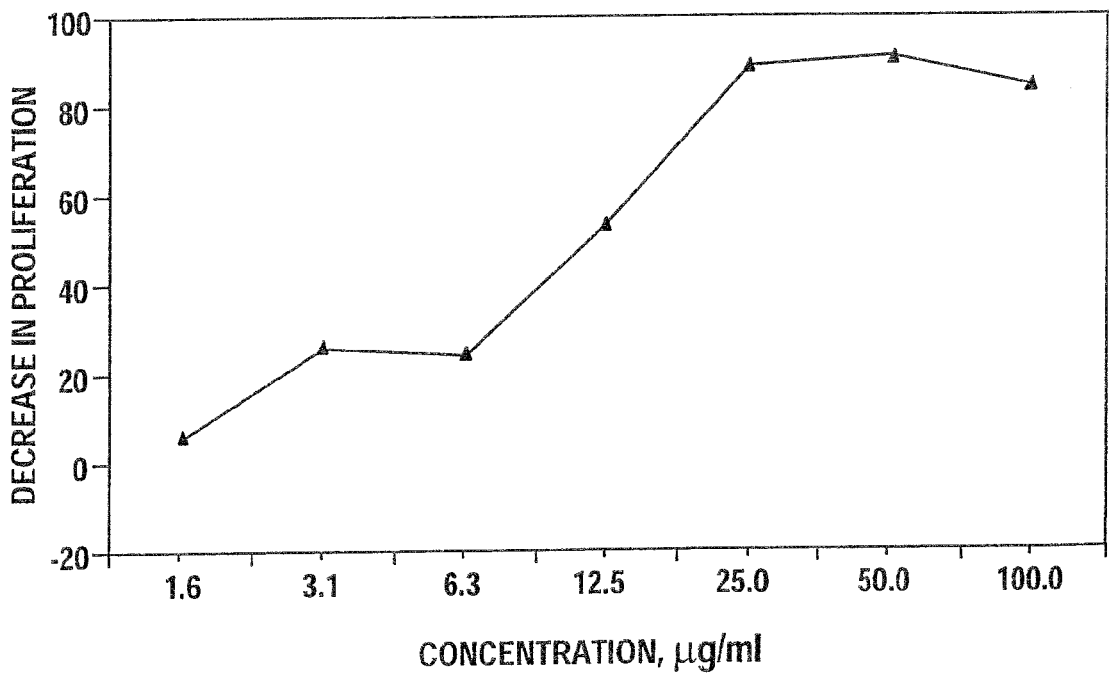
FIG. 8 is a graph that illustrates results of an experiment similar to the experiment of FIG. 7, except that the SK-Mel 28 human melanoma cells were cultured in media without serum. The graph in FIG. 8 comprises percentage decrease in cell proliferation on the y-axis, and concentration of a methanol extract of *Combretum laurifolium* Mart. on the x-axis.

An additional assay was conducted to determine the effect of the methanol extract on the proliferation of human cancer cells. The human melanoma cell line, SK-Mel 28, was used in two independent experiments. The methanol extract was administered to the SK-Mel 28 cells in differing concentrations ranging from 1.6 μg/ml to 100 μg/ml. The methanol extract was administered to SK-Mel 28 cells cultured in the presence and absence of human growth serum, since serum, which normally contains various growth factors, may interfere in the inhibition of SK-Mel 28 cell proliferation. Cell proliferation was measured by the CellTiter 96 Aqueous One Solution Cell Proliferation Assay (Promega Corporation, Madison, Wis.) that uses a tetrazolium compound [3-(4,5-dimethylthiazol-2-yl)-5-(3-carboxymethoxyphenyl)-2-(4-sulfophenyl)-2H-tetrazolium, innersalt, or "MTS"], in combination with an electron coupling reagent (phenazine ethosulfate, or "PES"), to produce a calorimetric change indicating cell proliferation. The assay measured the decrease in proliferation of SK-Mel 28 by the methanol extract by recording absorbance at 490 nm. The results of the assay are shown in FIGS. 7 and 8. FIG. 7 shows that the methanol extract at 100 µg/ml produced about a 30% decrease of the proliferation of human melanoma cell line SK-Mel 28 in growth medium supplemented with serum, with an IC50 of over 100 µg/ml. The decrease in proliferation of SK-Mel 28 by the methanol extract was also assayed in SK-Mel 28 cells in growth medium without serum, the results of which are shown in FIG. 8. A pronounced decrease of SK-Mel 28 cell proliferation by the methanol extract with an IC50 of 84 µg/ml was observed as shown in FIG. 8. Also, FIGS. 7-8 illustrate results showing that the methanol extract decreased the proliferation of SK-Mel 28 in a dose-dependent manner.

In order to identify the components of a methanol extract responsible for inhibition of COX-2, a methanol extract from *Combretum laurifolium* Mart. was fractionated on a semi-preparative column. The methanol extract was loaded onto an Agilent™ Zorbax™ XDB C18 21.2×100 mm Column using a CTC Analytics™ PAL™ injector (liquid chromatography automated injector), with an injection volume of 50 µl. The methanol extract was eluted using a Shimadzu™ LC-6™ binary high pressure system. The first mobile phase was $H_2O$ with 0.05% trifluoroacetic acid ("TFA"), and the second mobile phase was methanol with 0.05% TFA. A post-column split was employed having two Valco Y fittings with a 30 µm internal diameter ("id") by 15 cm long restriction capillary and an approximate split ratio of 500:1. The fraction collector was an Advantec, with time set based on fractionation starting at 0.8 min, and 0.20 min collection steps. Of course, other variables may be used to accomplish the same or similar fractionation. Fractions eluting at different times may be collected, dried under nitrogen or freeze-dried, resulting in relatively pure fractions. The dried fractions may be incorporated into a medicament to treat any disease or ailment which may be treated by inhibiting COX-2, including but not limited to diseases related to inflammation or cancer, according to methods known in the art.

Figure 9:
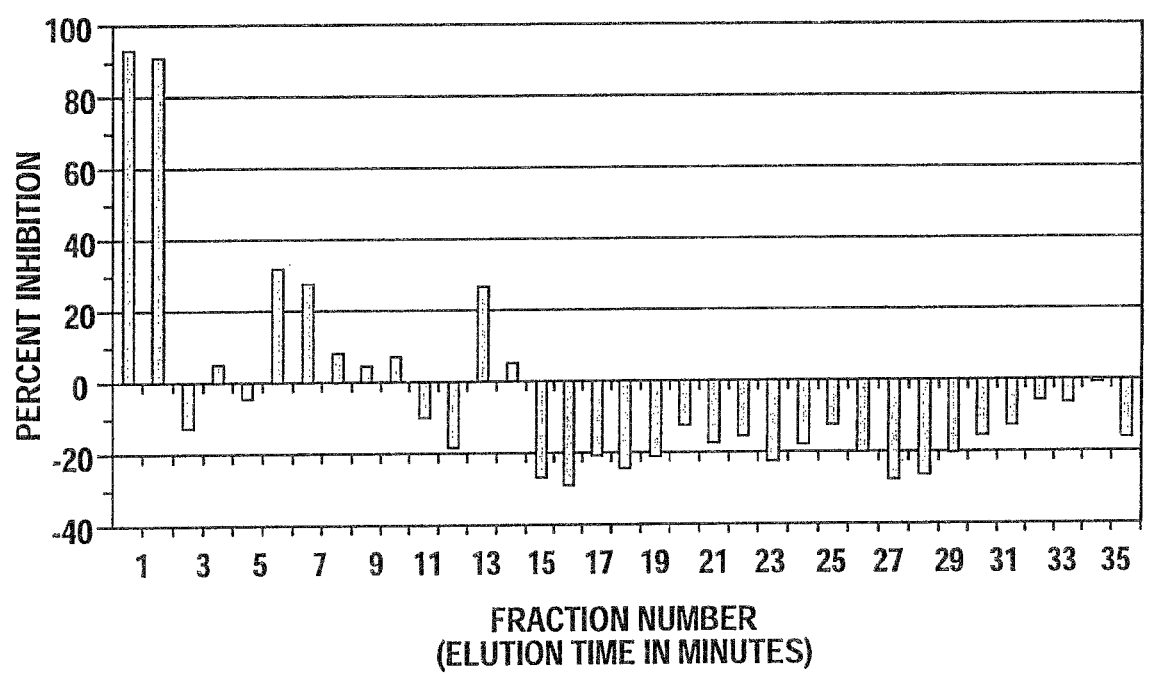
FIG. 9 is a graph that illustrates the results from an experiment to test the inhibition of COX-2 in vitro by fractions of a methanol extract of *Combretum laurifolium* Mart., at a concentration of 10 µg/ml, with percentage inhibition of human recombinant COX-2 on the y-axis, and fractions identified by elution time in minutes on the x-axis.
Figure 10A:
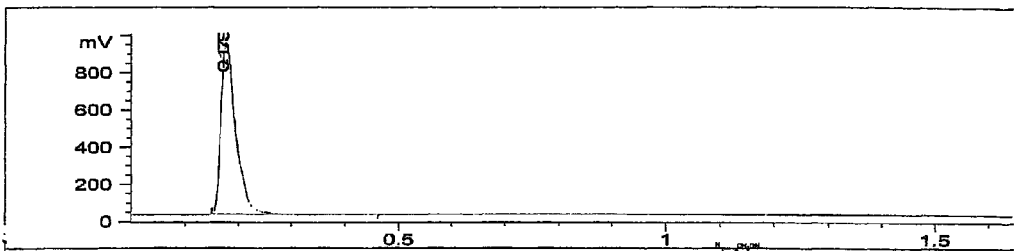
FIGS. 10A-10E are high pressure liquid chromatography profiles based on the liquid chromatography-mass spectrometry and mass detection pertaining to fractions 1 and 2 in FIG. 9 of the methanol extract of *Combretum laurifolium* Mart.
Figure 10B:
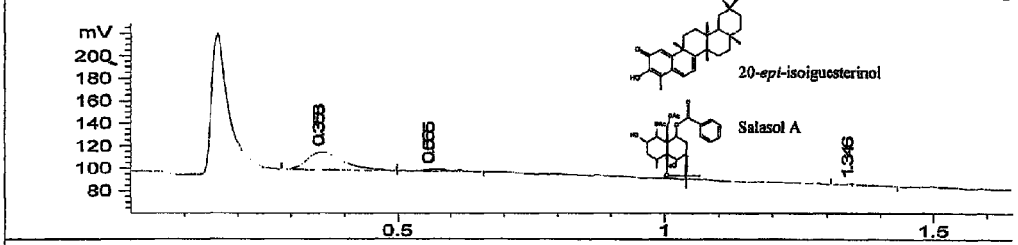
Figure 10C:
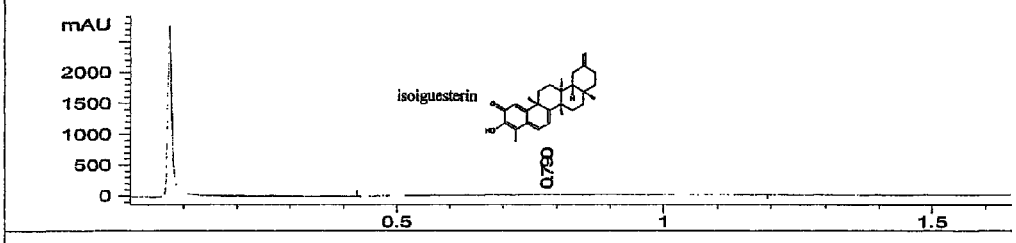
Figure 10D:
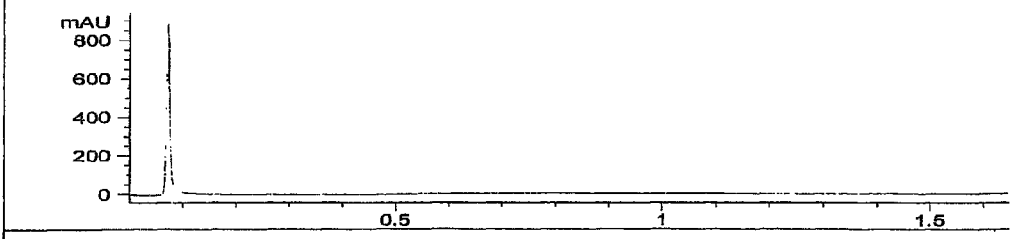
Figure 10E:
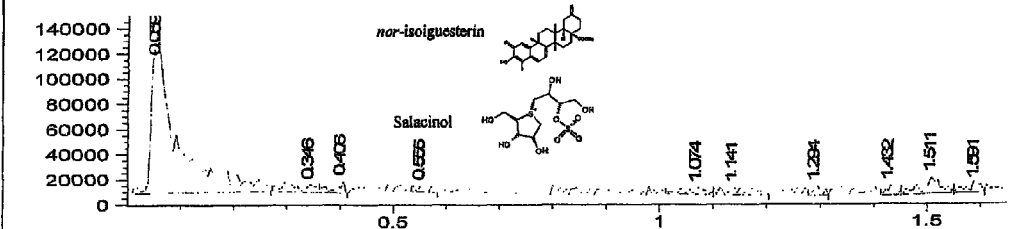

The inhibition of COX-2 by the fractions from the *Combretum laurifolium* Mart. methanol extract was examined by COX-2 Inhibition Assays. In order to prepare the dried fractions for a COX-2 Inhibition Assay, dried fractions were suspended in 100% DMSO and water for a concentration of 0.5% DMSO. A control with only 0.5% DMSO may be included in the COX-2 Inhibition Assay. The fractions were tested at varying concentrations such as, but not limited to, 1.56-100 µg/ml. The results of the COX-2 Inhibition Assay using the fractions from a *Combretum laurifolium* Mart. methanol extract, at a concentration of 10 µg/ml, are shown on FIG. 9. FIG. 9 shows fraction number by elution time in minutes on the x-axis (with elution time in minutes hereinafter being the identifying number of each fraction), and percentage inhibition of human recombinant COX-2 on the y-axis. As can be seen in FIG. 9, fractions 1 and 2, which eluted at one minute and two minutes, respectively, showed the most COX-2 inhibition, while fractions 6, 7 and 13 also showed significant COX-2 inhibition. Some inhibition was exhibited by fractions 4, 8, 9, 10 and 14.

The fractions that showed the most COX-2 inhibition, specifically fractions 1 and 2, were profiled for structure using analytical Liquid Chromatography-Mass Spectrometry ("LC-MS") on a hypersil C18 reverse phase column (100×2.1 mm, 5 mm) and eluted with a water-acetonitrile gradient on a flow rate of 0.6 ml/min. FIGS. 10A-10E show the mass spectra from fractions 1 and 2. As shown in FIGS. 10A-10E, components that may be present in fractions 1 and 2 include 20-epi-isoiguesterinol, Salasol A, isoguesterin, nor-isoguesterin, and salacinol.

Inhibition of NF-Kappa B Activation and an Extract of *Combretum laurifolium* Mart.

An NF-Kappa B assay demonstrated that an aqueous extract of *Combretum laurifolium* Mart., a methanol extract of *Combretum laurifolium* Mart., an ethyl-acetate extract of *Combretum laurifolium* Mart., and a hexane extract of *Combretum laurifolium* Mart. may decrease the inflammatory response in vitro in human embryonic kidney 293 cells. NF-Kappa B is a transcription factor. It is understood by persons of ordinary skill in the art that NF-Kappa B activation/expression is one of many early inflammatory responses and is an indicator of inflammation. Inhibition of NF-Kappa B activation may involve a corresponding inhibition of inflammation. Thus, an extract that inhibits NF-Kappa B activation may treat inflammation in a patient. FIGS. 15-23 show the results of NF-Kappa B report gene assays to test the effects of an aqueous extract, a methanol extract, a hexane extract, and an ethyl-acetate extract of *Combretum laurifolium* Mart. on NF-Kappa B activation. Human embryonic kidney 293 cells were transfected with a DNA plasmid containing a NF-Kappa B response element upstream of the firefly luciferase gene. If NF-Kappa B is activated, there is an increased luciferase expression. Luciferase expression is measured by an enzyme reaction in which the luciferase produces light. A greater degree of light corresponds with an increased NF-Kappa B activation.

Both TNF (tumor necrosis factor) and PMA (phorbol ester) are known potent activators of NF-Kappa B. For an NF-Kappa B assay, Human embryonic kidney 293 cells were plated in charcoal stripped media overnight. Human embryonic kidney 293 cells were exposed separately to DMSO only and PMA at a concentration of 20 ng/ml, and in a second experiment, DMSO only and TNF at a concentration of 50 ng/ml, and each of the foregoing treatment groups were given a dose range of an aqueous extract, a methanol extract, a hexane extract, or an ethyl-acetate extract of *Combretum laurifolium* Mart. dissolved in DMSO at 20 µg/ml, 2.0 µg/ml or 0.2 µg/ml. The cells were harvested and lysed the following day for luciferase assay. The percent activation of NF-Kappa B in each treatment group was observed. The activation of NF-Kappa B was normalized to 100% with respect to the control containing DMSO and the known activator (TNF or PMA).

Figure 15:
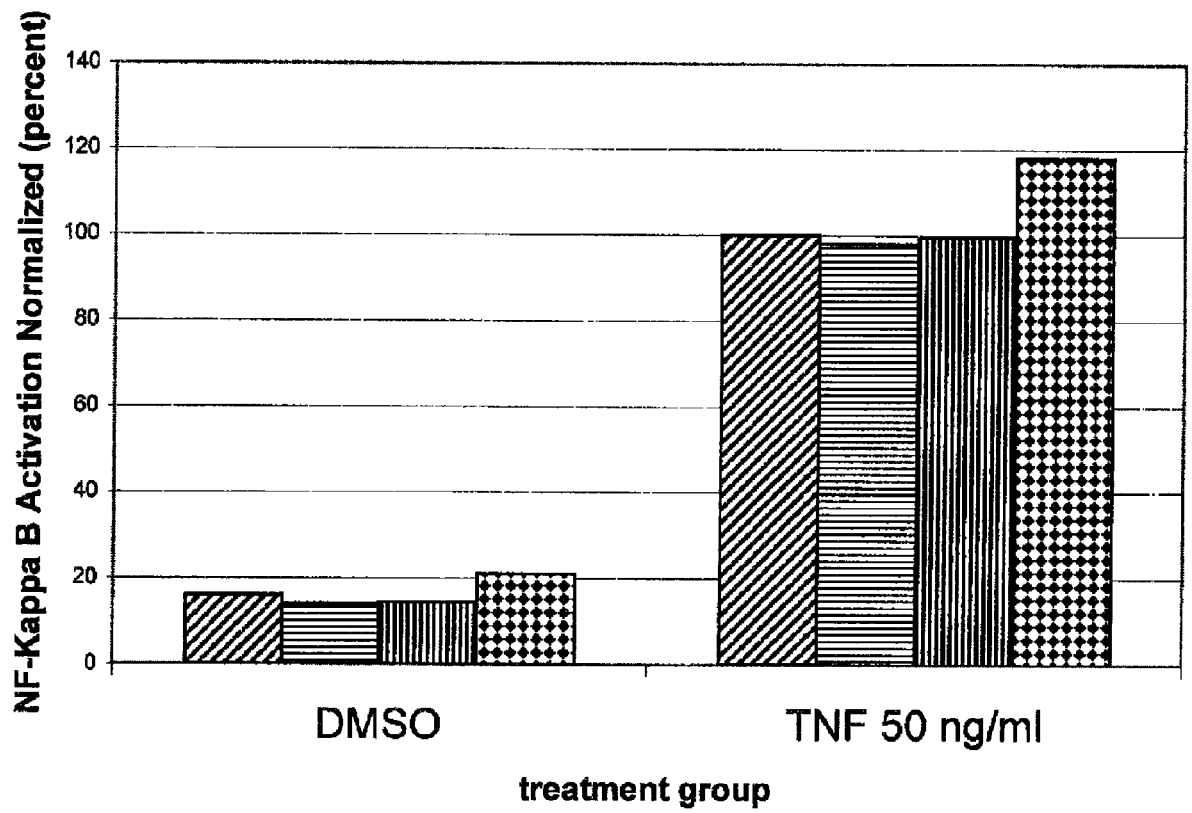
FIG. 15 is a graph that illustrates the results of an experiment to test NF-Kappa B activation in human embryonic kidney 293 cells exposed to an aqueous extract of *Combretum laurifolium* Mart. at varying concentrations and a known activator of NF-Kappa B, namely TNF. The graph in FIG. 15 comprises treatment group on the x-axis and NF-Kappa B activation normalized to the control (with no aqueous extract) to 100%.
Figure 16:
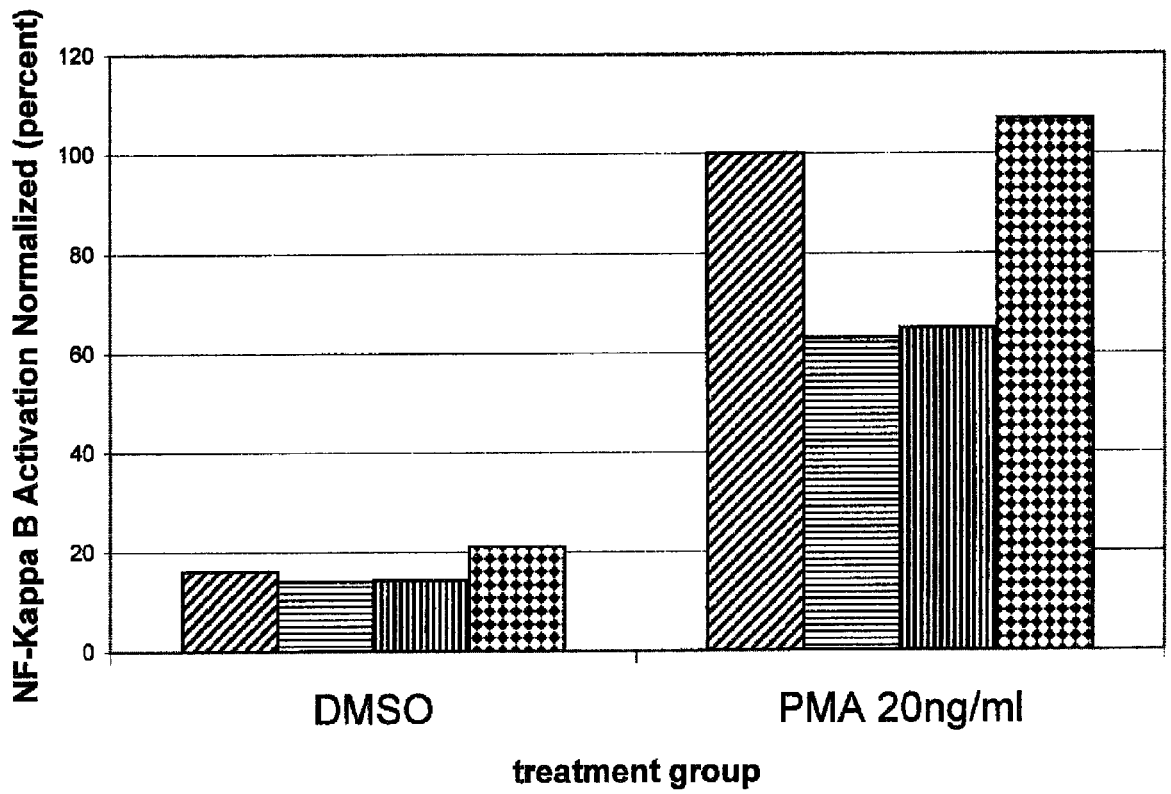
FIG. 16 is a graph that illustrates the results of an experiment to test NF-Kappa B activation in human embryonic kidney 293 cells exposed to an aqueous extract of *Combretum laurifolium* Mart. at varying concentrations and a known activator of NF-Kappa B, namely PMA. The graph in FIG. 16 comprises treatment group on the x-axis and NF-Kappa B activation normalized to the control (with no aqueous extract) to 100%.
Figure 21:
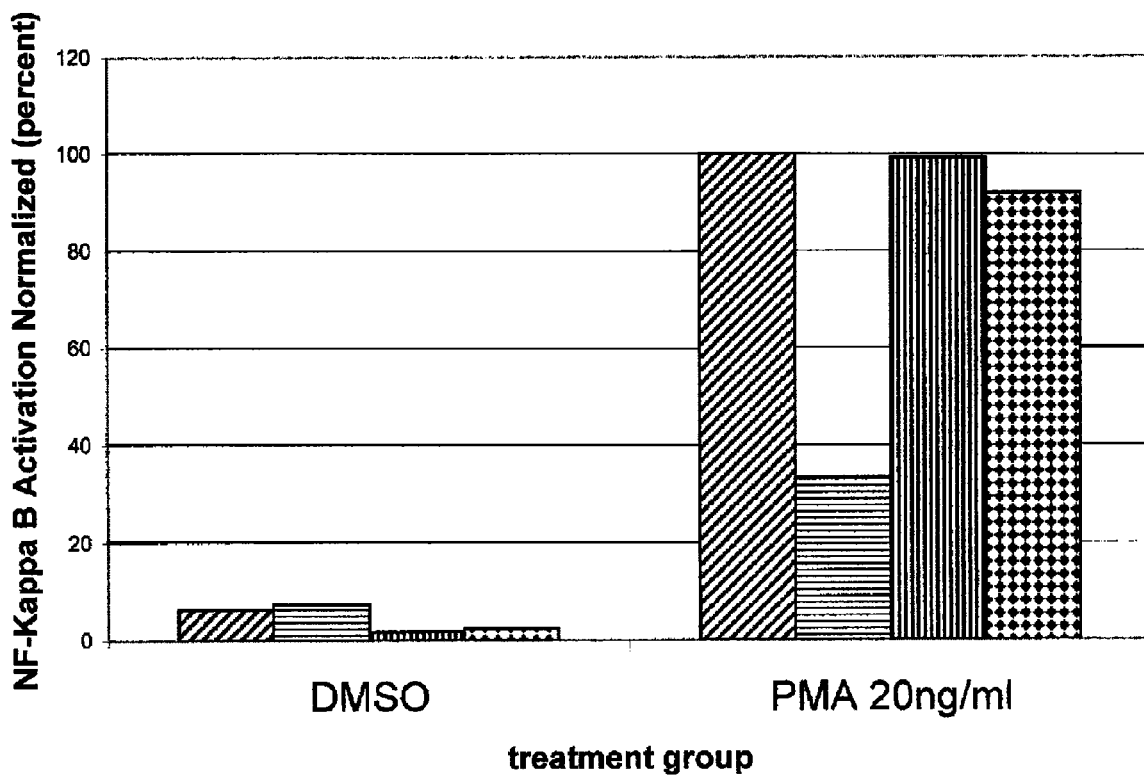
FIG. 21 is a graph that illustrates results of a replicate of the experiment of FIG. 16, namely an experiment to test NF-Kappa B activation in human embryonic kidney 293 cells exposed to an aqueous extract of *Combretum laurifolium* Mart. at varying concentrations and a known activator of NF-Kappa B, namely PMA. The graph in FIG. 21 comprises treatment group on the x-axis and NF-Kappa B activation normalized to the control (with no aqueous extract) to 100%.

The results from a NF-Kappa B assay using an aqueous extract of *Combretum laurifolium* Mart. are depicted in FIGS. 15, 16 and 21. FIG. 15 is a graph that illustrates the results from an experiment to test NF-Kappa B activation in cells administered TNF 50 ng/ml and an aqueous extract of *Combretum laurifolium* Mart. As illustrated in FIG. 15, in the TNF 50 ng/ml treatment group, the results were inconclusive as to NF-Kappa B activation. FIGS. 16 and 21 are graphs that illustrate the results from two separate experiments to test NF-Kappa B activation in cells administered PMA 20 ng/ml and an aqueous extract of *Combretum laurifolium* Mart. As illustrated in FIG. 16, in the PMA 20 ng/ml treatment group, NF-Kappa B activation was approximately 63% in cells administered an aqueous extract of *Combretum laurifolium* Mart. at 20 µg/ml and approximately 65% in cells administered an aqueous extract of *Combretum laurifolium* Mart. at 2 µg/ml. As illustrated in FIG. 21, in the PMA 20 ng/ml treatment group, NF-Kappa B activation was approximately 33% in cells administered an aqueous extract of *Combretum lau-*

*rifolium* Mart. at 20 µg/ml and approximately 91% in cells administered an aqueous extract of *Combretum laurifolium* Mart. at 0.2 µg/ml.

Figure 17:
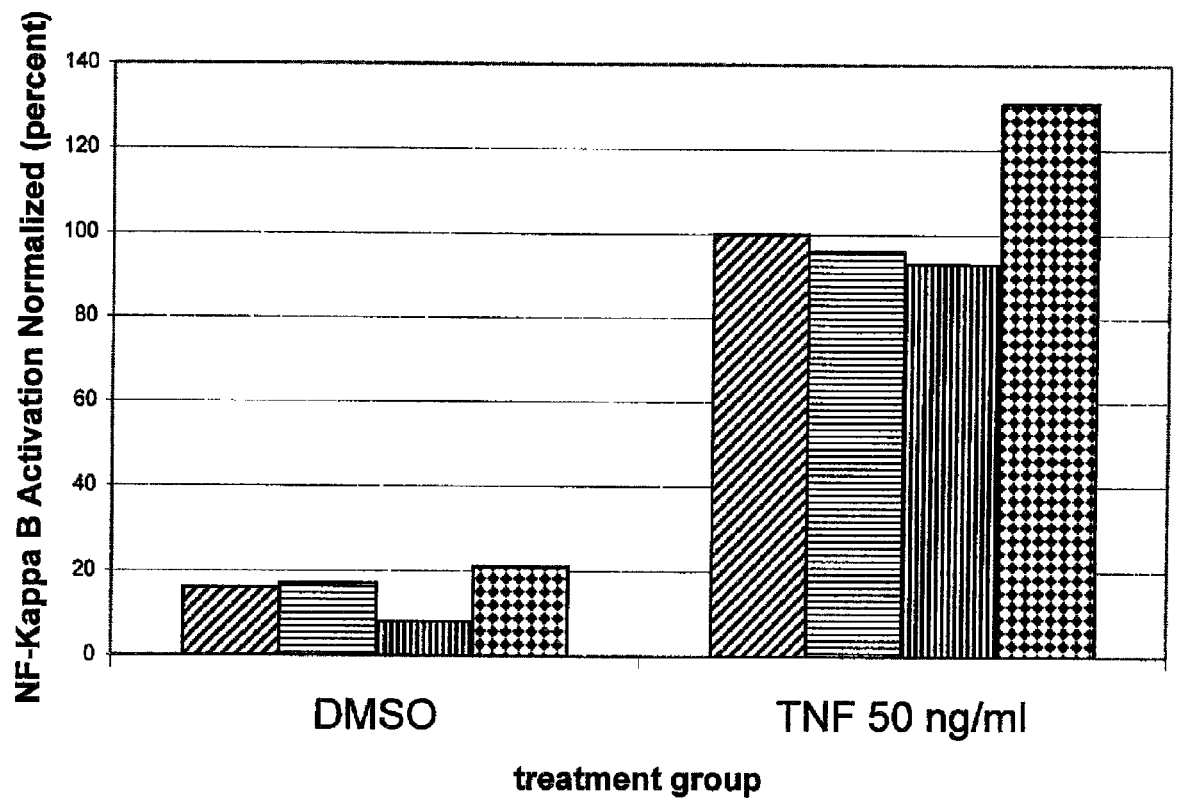
FIG. 17 is a graph that illustrates the results of an experiment to test NF-Kappa B activation in human embryonic kidney 293 cells exposed to a methanol extract of *Combretum laurifolium* Mart. at varying concentrations and a known activator of NF-Kappa B, namely TNF. The graph in FIG. 17 comprises treatment group on the x-axis and NF-Kappa B activation normalized to the control (with no methanol extract) to 100%.
Figure 18:
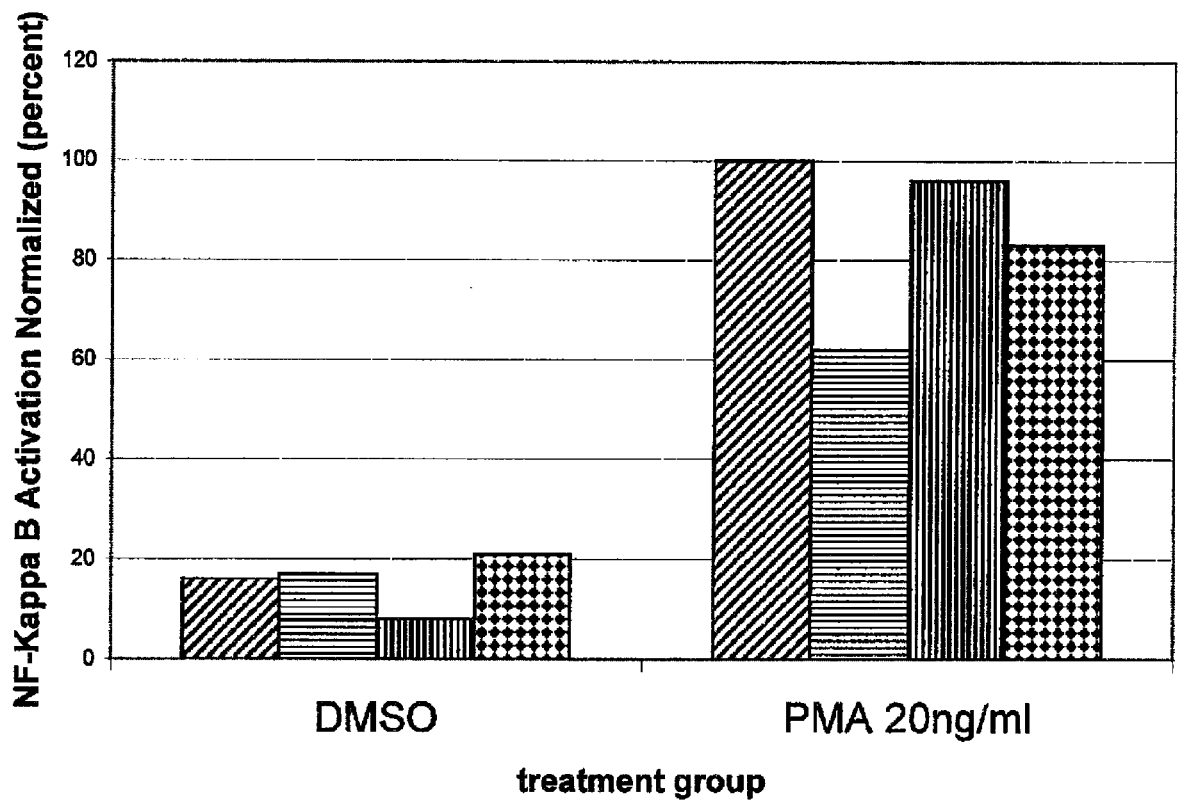
FIG. 18 is a graph that illustrates the results of an experiment to test NF-Kappa B activation in human embryonic kidney 293 cells exposed to a methanol extract of *Combretum laurifolium* Mart. at varying concentrations and a known activator of NF-Kappa B, namely PMA. The graph in FIG. 18 comprises treatment group on the x-axis and NF-Kappa B activation normalized to the control (with no methanol extract) to 100%.
Figure 19:
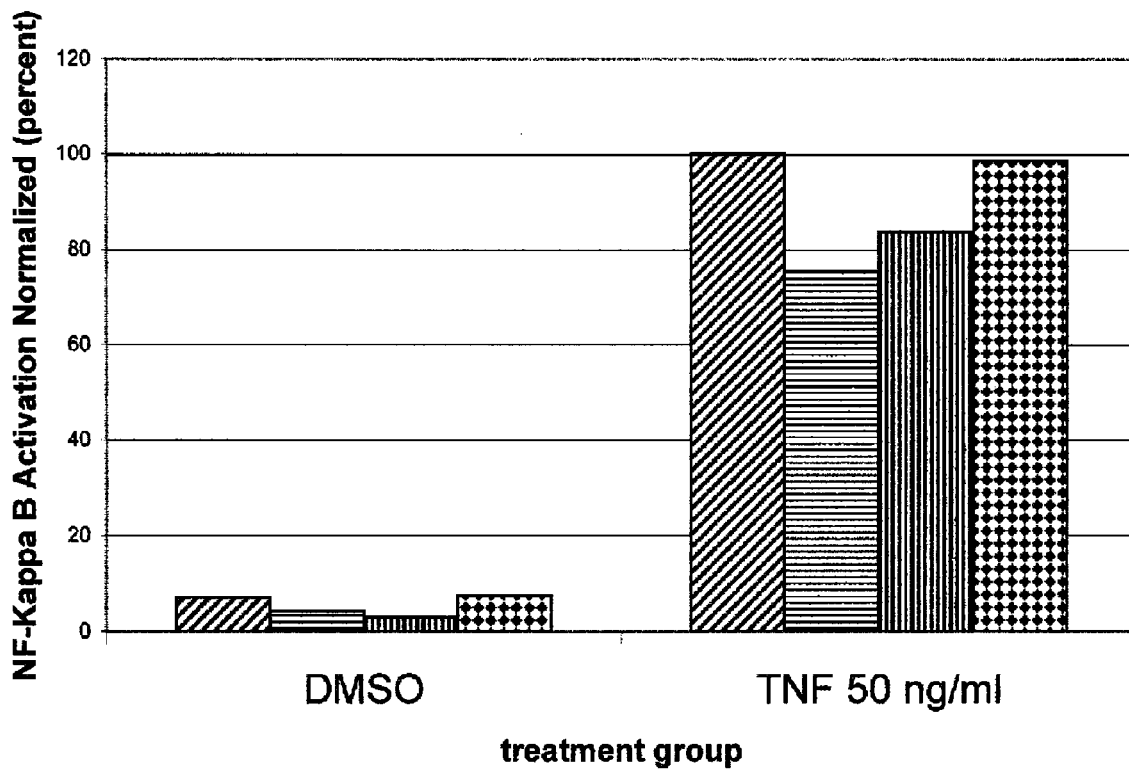
FIG. 19 is a graph that illustrates results of a replicate of the experiment of FIG. 17, namely an experiment to test NF-Kappa B activation in human embryonic kidney 293 cells exposed to a methanol extract of *Combretum laurifolium* Mart. at varying concentrations and a known activator of NF-Kappa B, namely TNF. The graph in FIG. 19 comprises treatment group on the x-axis and NF-Kappa B activation normalized to the control (with no methanol extract) to 100%.
Figure 20:
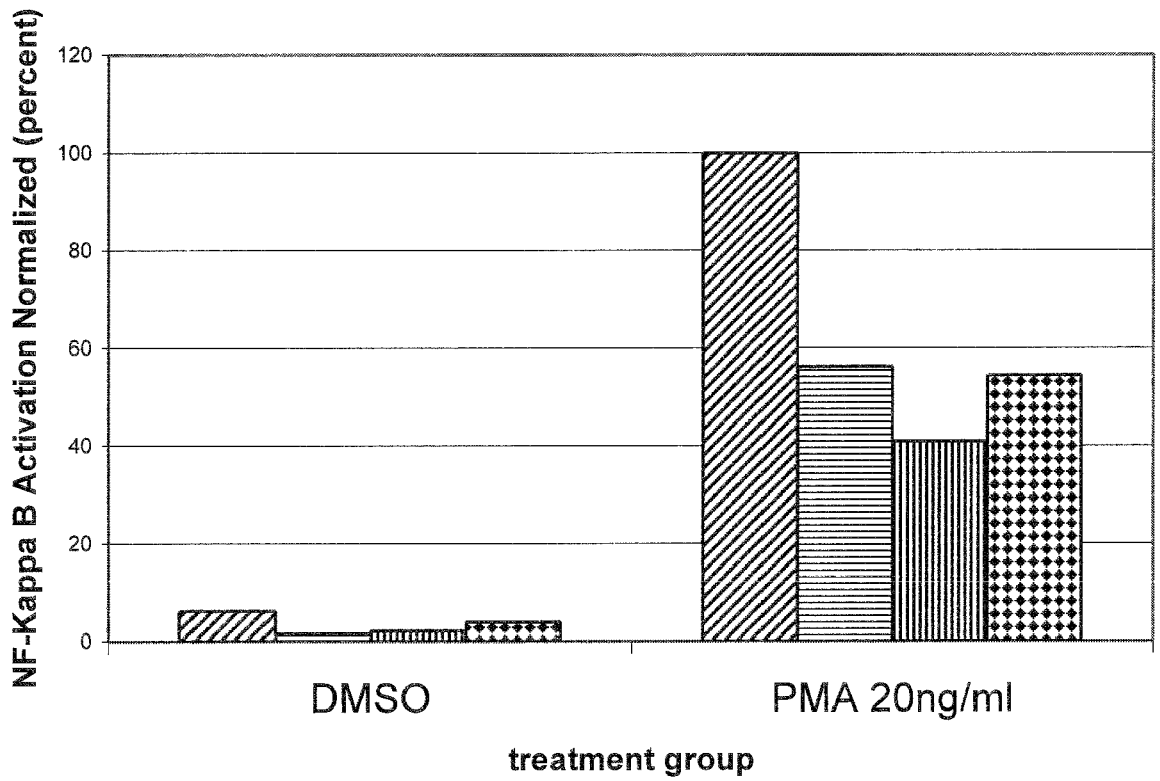
FIG. 20 is a graph that illustrates results of a replicate of the experiment of FIG. 18, namely an experiment to test NF-Kappa B activation in human embryonic kidney 293 cells exposed to a methanol extract of *Combretum laurifolium* Mart. at varying concentrations and a known activator of NF-Kappa B, namely PMA. The graph in FIG. 20 comprises treatment group on the x-axis and NF-Kappa B activation normalized to the control (with no methanol extract) to 100%.

FIGS. 17 and 19 are graphs that illustrate the results from two separate experiments to test NF-Kappa B activation in cells administered TNF 50 ng/ml and methanol extract of *Combretum laurifolium* Mart. FIG. 17 is a graph that illustrates the results from an experiment to test NF-Kappa B activation in cells administered TNF 50 ng/ml and a methanol extract of *Combretum laurifolium* Mart. As illustrated in FIG. 17, in the TNF 50 ng/ml treatment group, NF-Kappa B activation was approximately 96% in cells administered a methanol extract of *Combretum laurifolium* Mart. at 20 µg/ml, approximately 93% in cells administered a methanol extract of *Combretum laurifolium* Mart. at 2 µg/ml. As illustrated in FIG. 19, in the TNF 50 ng/ml treatment group, NF-Kappa B activation was approximately 75% in cells administered a methanol extract of *Combretum laurifolium* Mart. at 20 µg/ml, approximately 84% in cells administered a methanol extract of *Combretum laurifolium* Mart. at 2 µg/ml and approximately 98% in cells administered a methanol extract of *Combretum laurifolium* Mart. at 0.2 µg/ml. FIGS. 18 and 20 are graphs that illustrate the results from two separate experiments to test NF-Kappa B activation in cells administered PMA 20 ng/ml and a methanol extract of *Combretum laurifolium* Mart. As illustrated in FIG. 18, in the PMA 20 ng/ml treatment group, NF-Kappa B activation was approximately 62% in cells administered a methanol extract of *Combretum laurifolium* Mart. at 20 µg/ml, approximately 96% in cells administered a methanol extract of *Combretum laurifolium* Mart. at 2 µg/ml, and approximately 83% in cells administered a methanol extract of *Combretum laurifolium* Mart. at 0.2 µg/ml. As illustrated in FIG. 20, in the PMA 20 ng/ml treatment group, NF-Kappa B activation was approximately 56% in cells administered a methanol extract of *Combretum laurifolium* Mart. at 20 µg/ml, approximately 40% in cells administered a methanol extract of *Combretum laurifolium* Mart. at 2 µg/ml, and approximately 54% in cells administered a methanol extract of *Combretum laurifolium* Mart. at 0.2 µg/ml.

Figure 22:
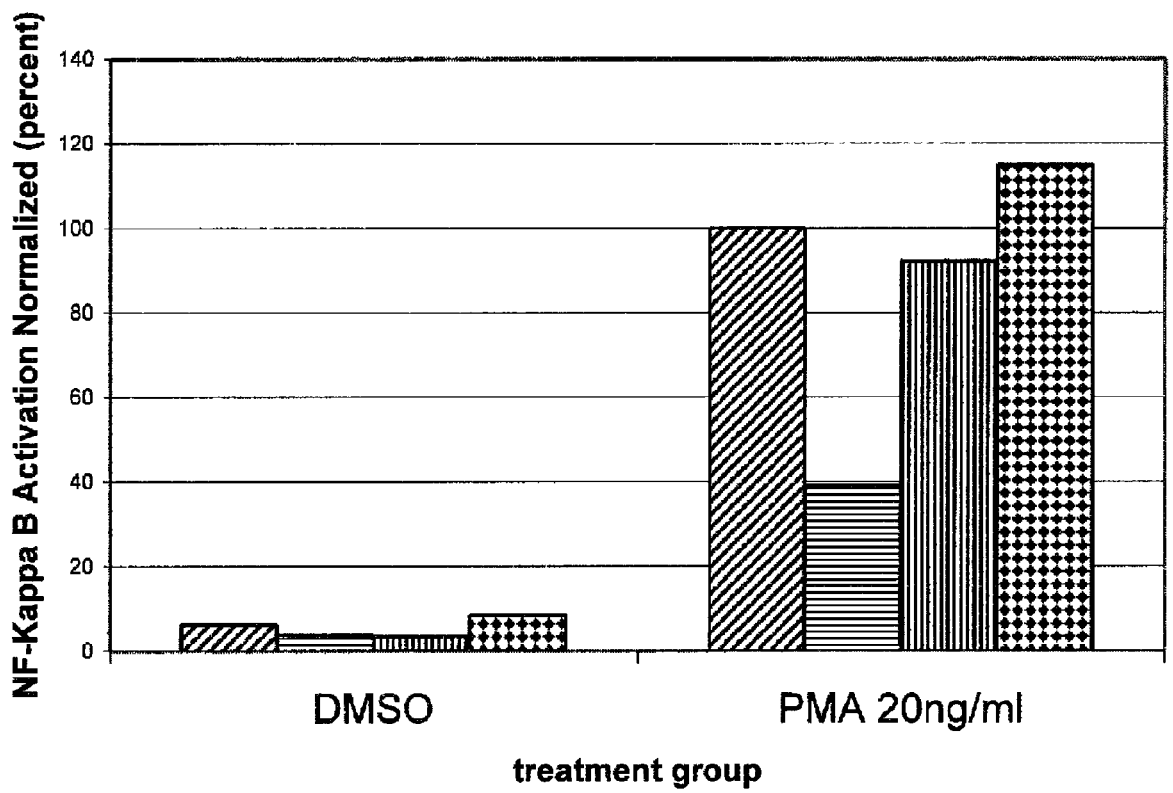
FIG. 22 is a graph that illustrates the results of an experiment to test NF-Kappa B activation in human embryonic kidney 293 cells exposed to a hexane extract of *Combretum laurifolium* Mart. at varying concentrations and a known activator of NF-Kappa B, namely PMA. The graph in FIG. 22 comprises treatment group on the x-axis and NF-Kappa B activation normalized to the control (with no hexane extract) to 100%.

The results from a NF-Kappa B assay using a hexane extract of *Combretum laurifolium* Mart. are depicted in FIG. 22. FIG. 22 is a graph that illustrates the results from an experiment to test NF-Kappa B activation in cells administered PMA 20 ng/ml and a hexane extract of *Combretum laurifolium* Mart. As illustrated in FIG. 22, in the PMA 20 ng/ml treatment group, NF-Kappa B activation was approximately 39% in cells administered a hexane extract of *Combretum laurifolium* Mart. at 20 µg/ml and approximately 92% in cells administered an aqueous extract of *Combretum laurifolium* Mart. at 2 µg/ml. The results from an NF-Kappa B assay using a hexane extract of *Combretum laurifolium* Mart. and TNF 50 ng/ml were inconclusive.

Figure 23:
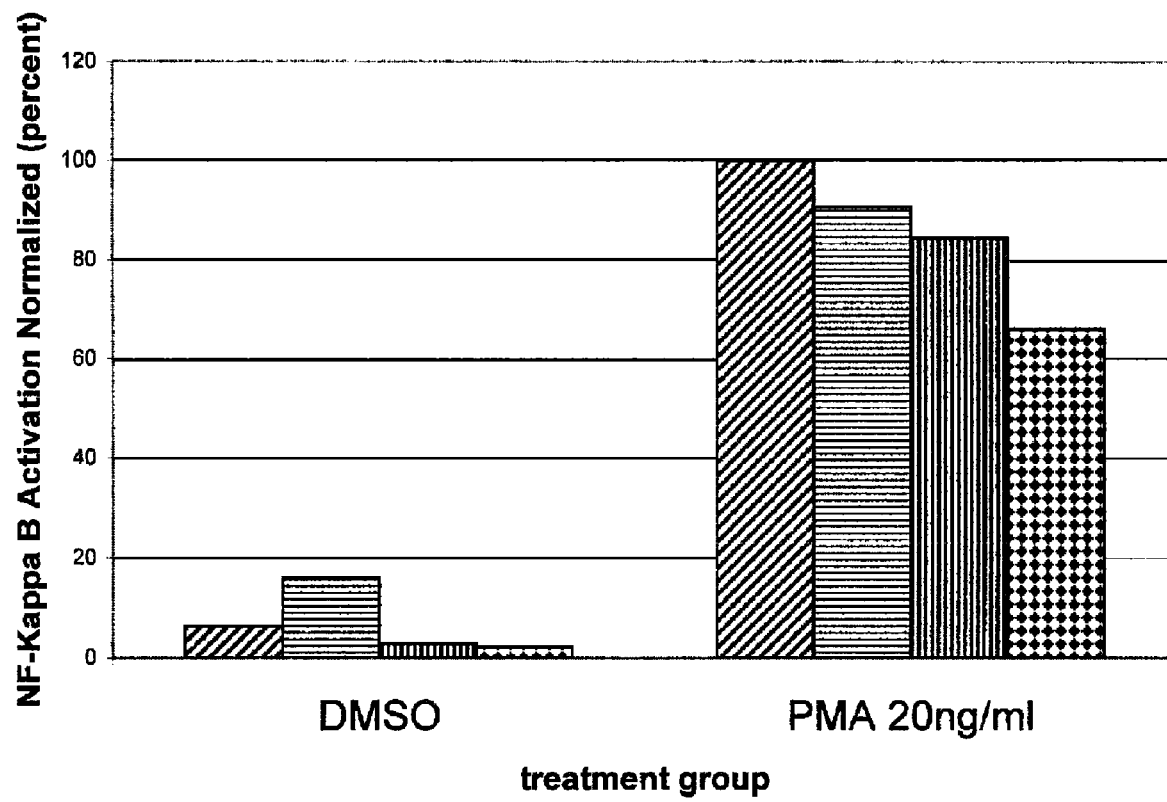
FIG. 23 is a graph that illustrates the results of an experiment to test NF-Kappa B activation in human embryonic kidney 293 cells exposed to an ethyl-acetate extract of *Combretum laurifolium* Mart. at varying concentrations and a known activator of NF-Kappa B, namely PMA. The graph in FIG. 23 comprises treatment group on the x-axis and NF-Kappa B activation normalized to the control (with no ethyl-acetate extract) to 100%.

The results from a NF-Kappa B assay using an ethyl-acetate extract of *Combretum laurifolium* Mart. are depicted in FIG. 23. FIG. 23 is a graph that illustrates the results from an experiment to test NF-Kappa B activation in cells administered PMA 20 ng/ml and an ethyl-acetate extract of *Combretum laurifolium* Mart. As illustrated in FIG. 23, in the PMA 20 ng/ml treatment group, NF-Kappa B activation was approximately 91% in cells administered a ethyl-acetate extract of *Combretum laurifolium* Mart. at 20 µg/ml, approximately 84% in cells administered an ethyl-acetate extract of *Combretum laurifolium* Mart. at 2 µg/ml and approximately 66% in cells administered an ethyl-acetate extract of *Combretum laurifolium* Mart. at 0.2 µg/ml. The results from an NF-Kappa B assay using an ethyl-acetate extract of *Combretum laurifolium* Mart. and TNF 50 ng/ml were inconclusive.

An Extract of *Combretum laurifolium* Mart. and a Decrease in Cancer Growth

Figure 11:
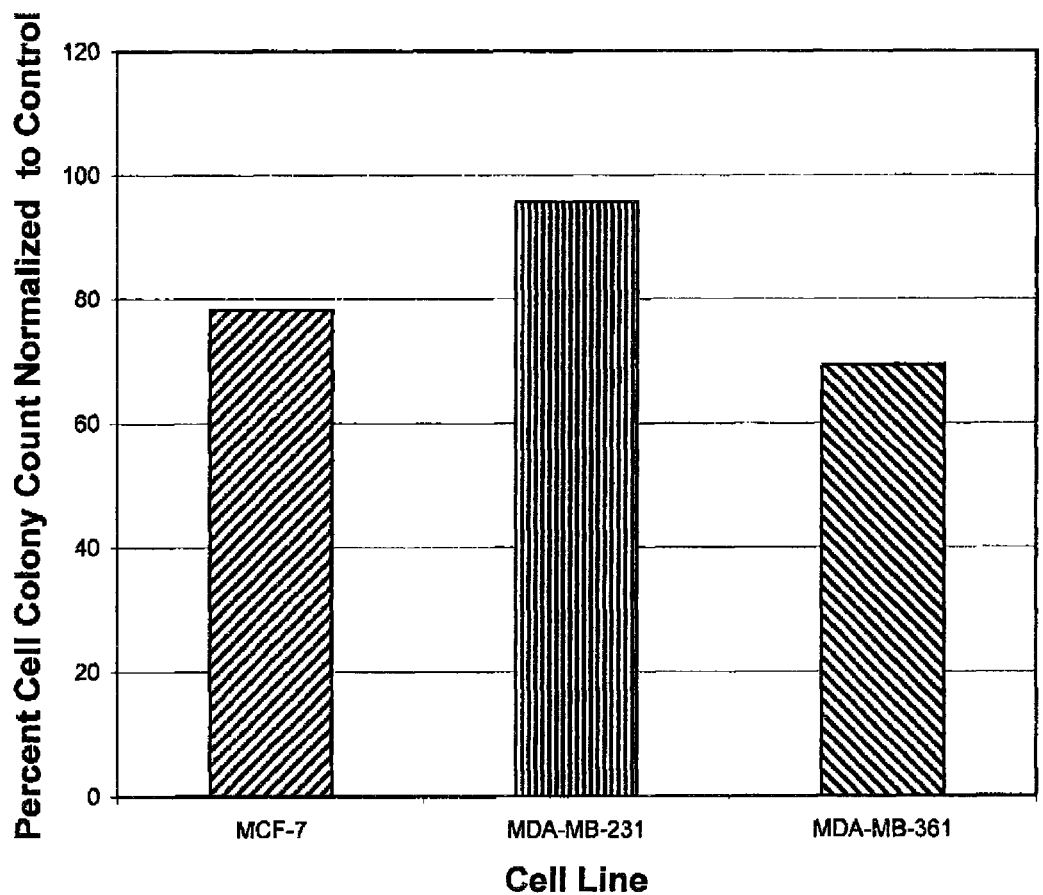
FIG. 11 is a graph that illustrates the results from an experiment to test the cell colony number of three breast cancer cell lines administered a methanol extract of *Combretum laurifolium* Mart. The graph in FIG. 11 comprises cell line on the x-axis and percent cell colony count normalized with the control to 100% on the y-axis.
Figure 11:
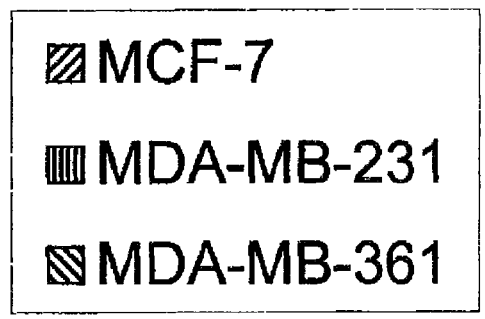
Figure 12:
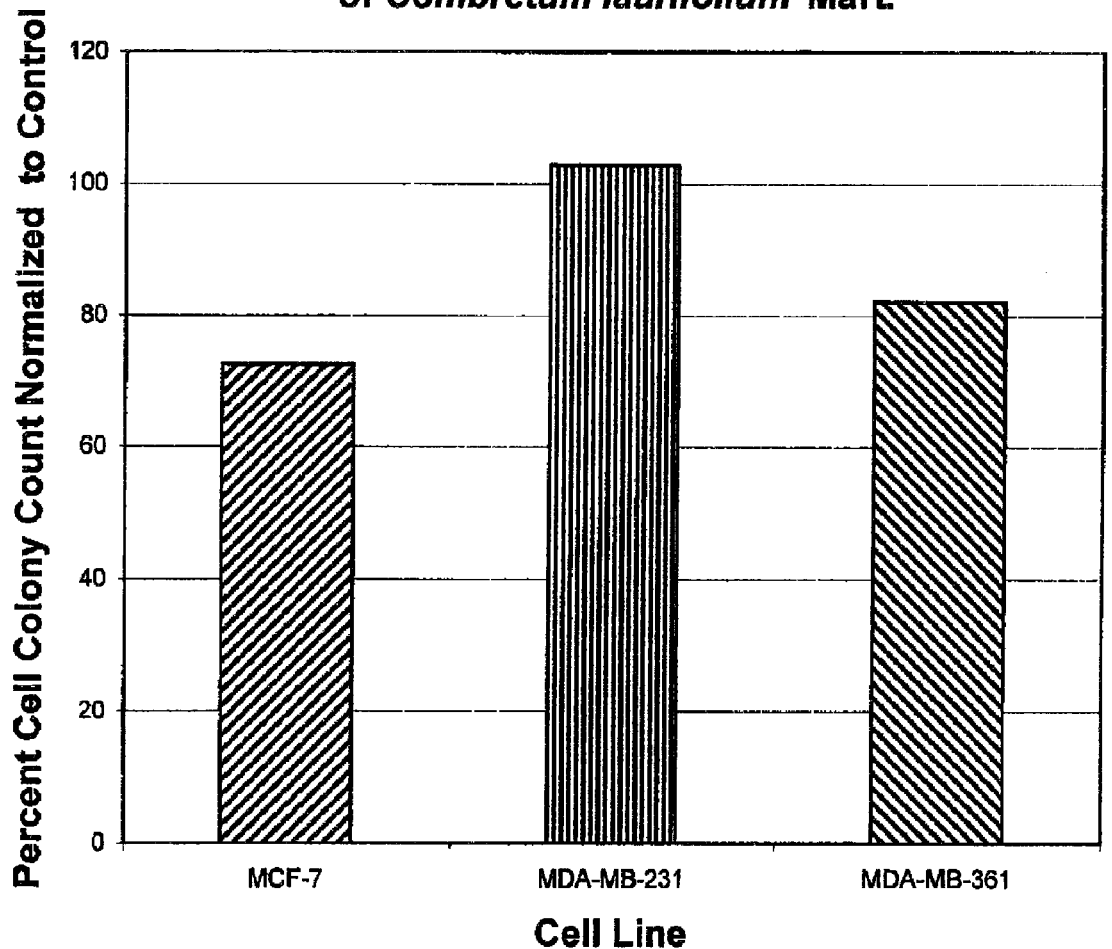
FIG. 12 is a graph that illustrates the results from an experiment to test the cell colony number of three breast cancer cell lines administered a hexane extract of *Combretum laurifolium* Mart. The graph in FIG. 12 comprises cell line on the x-axis and percent cell colony count normalized with the control to 100% on the y-axis.
Figure 12:

An in vitro cell culture assay demonstrated that a methanol extract of *Combretum laurifolium* Mart. and a hexane extract of *Combretum laurifolium* Mart. decrease the growth of cell colony formation in cancer cell lines. The results from an in vitro cell culture assay with an aqueous extract of *Combretum laurifolium* Mart. and an ethyl-acetate extract of *Combretum laurifolium* Mart. were inconclusive. FIG. 11 and FIG. 12 depict results using three breast cancer cell lines: MCF-7 (an estrogen receptor positive human breast cancer cell line), human breast cancer cell line MDA-MB-231 (an estrogen independent cancer cell line that originated from a human metastatic ductal breast carcinoma sample), and MDA-MB-361 (an estrogen receptor positive human breast cancer cell line derived from cerebral metastatic tissue) and a methanol extract of *Combretum laurifolium* Mart. or a hexane extract of *Combretum laurifolium* Mart.

Cells of the human breast cancer cell lines MCF-7, MDA-MB-231, MDA-MB-361 were seeded onto culture plates in media supplemented with serum. The cells were exposed to a methanol extract of *Combretum laurifolium* Mart. or a hexane extract of *Combretum laurifolium* Mart. dissolved in DMSO at a concentration of 10 µg/ml. A 7-10 day growth assay was performed. Cell growth was monitored by counting the cell colonies by staining the colonies and manually counting, with 50 cells equaling one colony. In the graph in FIG. 11, the results represent the number of cells that survive early exposure to a methanol extract of *Combretum laurifolium* Mart. and grow to form visible colonies. In FIG. 12, the results represent the number of cells that survive early exposure to a hexane extract of *Combretum laurifolium* Mart. and grow to form visible colonies. The raw colony count (number of colonies) for each cell line was normalized with the control for that treatment group (100%). The normalized cell colony count for each cell line exposed to a methanol extract of *Combretum laurifolium* Mart. is represented in FIG. 11, where each bar is the average of duplicate samples in that particular cell line exposed to a methanol extract of *Combretum laurifolium* Mart. The graph in FIG. 11 comprises cell line on the x-axis and cell colony count normalized with the control to 100% on the y-axis. As shown in FIG. 11, the methanol extract of *Combretum laurifolium* Mart. inhibited the growth of MDA-MB-361 to the greatest extent as compared to the other cell lines, showing approximately 69.3% normalized cell colony count, with the growth of MCF-7 having a normalized cell colony count of approximately 78.2%, and MDA-MB-231 having a normalized cell colony count of approximately 95.7%. The normalized cell colony count for each cell line exposed to a hexane extract of *Combretum laurifolium* Mart. is represented in FIG. 12, where each bar is the average of duplicate samples in that particular cell line exposed to a hexane extract of *Combretum laurifolium* Mart. The graph in FIG. 12 comprises cell line on the x-axis and cell colony count normalized with the control to 100% on the y-axis. As shown in FIG. 12, the hexane extract of *Combretum laurifolium* Mart. inhibited the growth of MCF-7 to the greatest extent as compared to the other cell lines, showing approximately 72.6% normalized cell colony count, with the growth of MDA-MB-361 having a normalized cell colony count of approximately 82.1%, and MDA-MB-231 having a normalized cell colony count of approximately 102.1%.

Experimental results demonstrate that a methanol extract of *Combretum laurifolium* Mart. may suppress breast cancer tumor growth in vivo. Female nude mice were each injected with 100 µl Reduced Growth Factor Matrigel from BD Biosciences™ and either $5 \times 10^6$ MCF-7 cells (estrogen receptor positive human breast carcinoma cells) at two subcutaneous dorsal sites or $5 \times 10^6$ MDA-MB-231 on their mammary fat pad, with the foregoing all suspended in 50 µl Phosphate Buffered Saline ("PBS"). Following tumor formation, which occurred at approximately 12 days post injection for mice injected with MDA-MB-231 cells and 10 days post injection for mice injected with MCF-7 cells, the nude mice were randomized into treatment groups. One group of nude mice were injected intraperitoneally ("IP") daily with a methanol extract of *Combretum laurifolium* Mart. suspended in a 50 μl 1:5 DMSO:PBS solution. Prior to suspension in the DMSO:PBS solution, the dried methanol extract was re-suspended in pure ethanol, aliquoted, and the ethanol was allowed to evaporate, leaving a dry powder. A control group of nude mice were treated with the 1:5 DMSO:PBS solution ("control") only. The nude mice were administered either the control or the methanol extract of *Combretum laurifolium* Mart. Tumors were measured every other day. Tumor volume was calculated by measuring the short and long axis of the tumor with calipers in millimeters, and using the equation 4.19×(Long axis/2)×(short axis/2)2 to arrive at tumor volume in cubic millimeters ($mm^3$). The tumor volume values were normalized.

Figure 13:
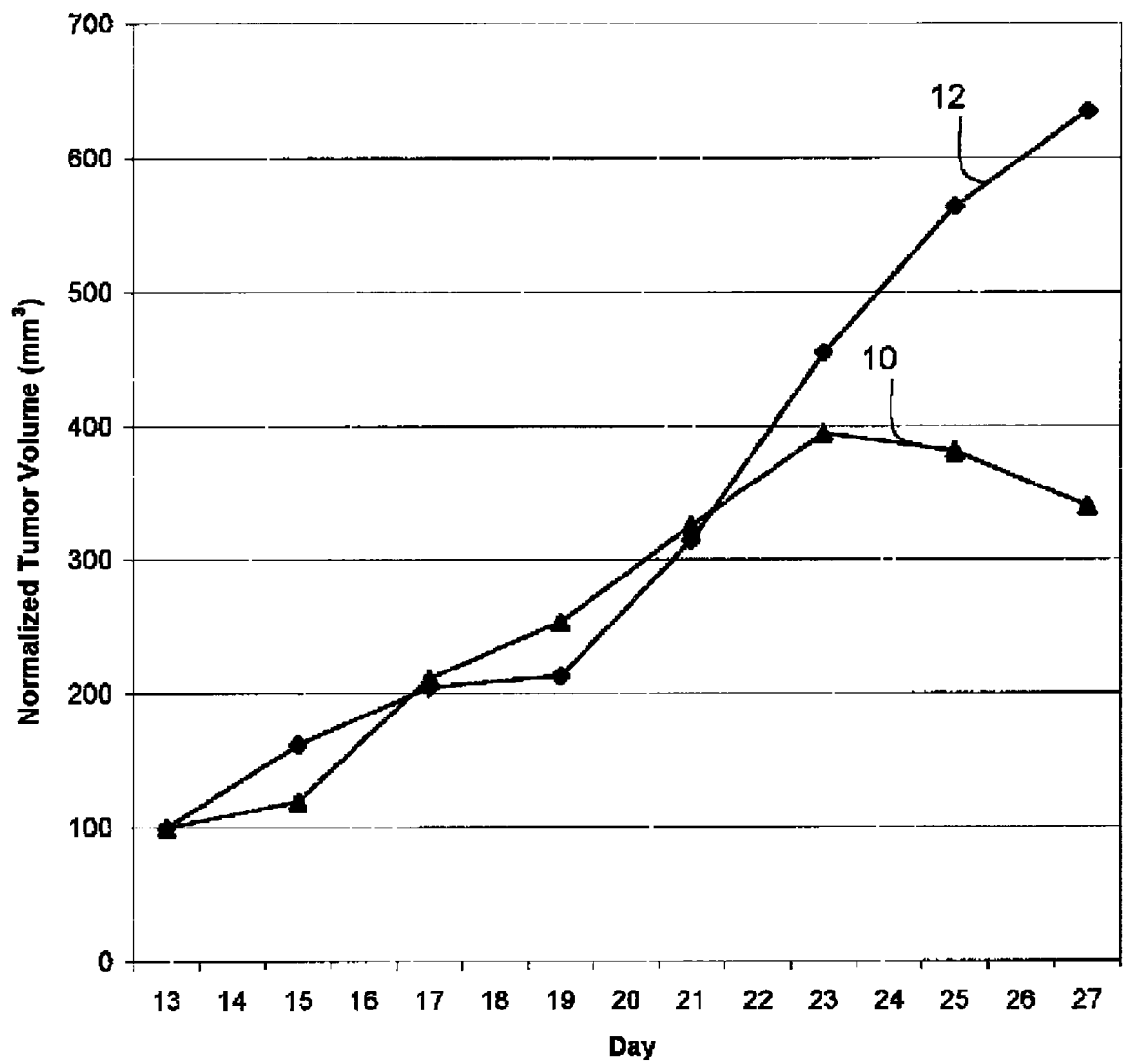
FIG. 13 is a graph that illustrates the results from an experiment to test the suppression of tumor growth in nude mice by a methanol extract of *Combretum laurifolium* Mart. administered intraperitoneally at a concentration of 8 mg/ml. The graph in FIG. 13 comprises normalized tumor volume on the y-axis and day post-injection of MDA-MB-231 cells on the x-axis.
Figure 14:
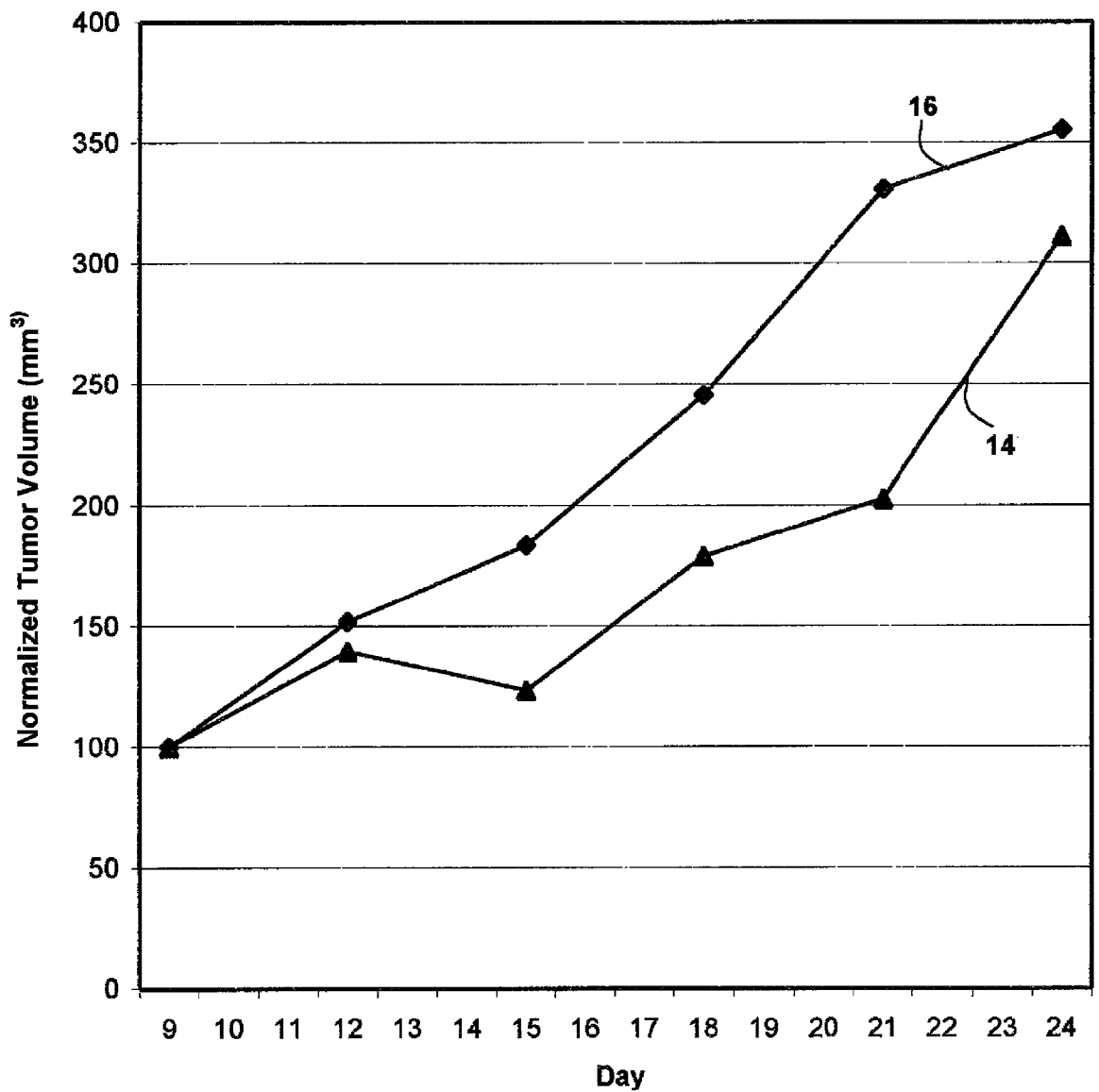
FIG. 14 is a graph that illustrates the results from an experiment to test the suppression of tumor growth in nude mice by a methanol extract of *Combretum laurifolium* Mart. administered intraperitoneally at a concentration of 8 mg/ml. The graph in FIG. 13 comprises normalized tumor volume on the y-axis and day post-injection of MCF-7 cells on the x-axis.

The results from two experiments using the foregoing methods are depicted in FIGS. 13 and 14, with normalized tumor volume on the y-axis in $mm^3$ and day post-injection of MDA-MB-231 cells or MCF-7 cells on the x-axis. Mice were injected on their mammary fat pad with MDA-MB-231 cells in the experiment depicted in FIG. 13, with 8 mice in the control group and 8 mice in the group administered a methanol extract of *Combretum laurifolium* Mart. at a final concentration of 0.8 mg/ml, each for 9 consecutive days. Starting 21 days post injection, the final concentration of the methanol extract of *Combretum laurifolium* Mart. was increased to 8 mg/ml in the group of mice being treated with the methanol extract. Tumors were measured every other day starting 13 days post injection. Plot line 10 represents the results from 8 nude mice that were administered the methanol extract of *Combretum laurifolium* Mart., and plot line 12 represents the results from 8 nude mice that were administered the control. In the experiment depicted in FIG. 14, 10 female nude mice were injected with MCF-7 cells at two subcutaneous dorsal sites in addition to having 0.72 mg.-60 day release estrogen pellets placed subscapular behind their ears. Plot line 14 represents the results from 5 nude mice that were administered a methanol extract of *Combretum laurifolium* Mart. at a concentration of 8 mg/ml, and plot line 16 represents the results from 5 nude mice that were administered the control, each starting at 10 days post injection. As shown in FIGS. 13-14, the methanol extract of *Combretum laurifolium* Mart. suppressed tumor growth as compared to the control.

It is understood by a person of ordinary skill in the art that a component that treats a condition by intraperitoneal injection is likely to treat a condition if administered parenterally. An extract of *Combretum laurifolium* Mart. may be administered to a patient parenterally to treat breast cancer.

An extract of *Combretum laurifolium* Mart. may be created using the methods described herein. Methanol or some other solvent, such as but not limited to a polar, non-polar, moderately polar or aqueous solvent, may be used to extract the components of *Combretum laurifolium* Mart. that at least partially inhibit COX-2. It is understood by persons of ordinary skill in the art that inhibiting COX-2 results in a decrease in inflammation, as COX-2 is an enzyme that contributes to the immune response generally referred to as inflammation. It is also understood by persons of ordinary skill in the art that inhibiting COX-2 results in apoptosis of cancer cells or a decrease in the proliferation of cancer cells. As such, an extract of *Combretum laurifolium* Mart. may be incorporated into a medicament and would be expected to treat cancer by either decreasing the proliferation of cancer cells or inducing the apoptosis of cancer cells. Such an extract may also be concentrated or dried and incorporated into a medicament. Alternatively, such an extract may be fractionated in order to further isolate certain fractions that inhibit COX-2. For example and without limitation, fractions 1-2 and fractions 6, 7 and 13, in any combination or individually, may be incorporated into a medicament to at least partially inhibit COX-2 in patients.

It is expected that a medicament containing an extract of *Combretum laurifolium* Mart. may be administered in a therapeutically effective amount to a patient to treat inflammation or to treat cancer. A medicament may be prepared containing an extract of *Combretum laurifolium* Mart. and formulated to administer to a patient by procedures known by a person of ordinary skill in the art.

A medicament containing an extract of *Combretum laurifolium* Mart. may be prepared by conventional procedures, known by a person of ordinary skill in the art, for blending and mixing compounds. For example, a methanol extract of *Combretum laurifolium* Mart., or fractions from a methanol extract of *Combretum laurifolium* Mart. such as fractions 1-2 or fractions 6, 7 and 13 alone or in combination, may be formulated into a therapeutically effective amount into a solution, a suspension, a powder, a capsule, a tablet, or a liquid, by use of a pharmaceutically acceptable vehicle to facilitate oral or enteral administration of the extract to treat a patient. Alternatively, an extract of *Combretum laurifolium* Mart. or particular fractions of an extract of *Combretum laurifolium* Mart. may be incorporated into a pharmaceutically acceptable vehicle to facilitate parenteral administration, including intravenous, intradermal, intramuscular, and subcutaneous administrations. In an alternative embodiment, an extract from *Combretum laurifolium* Mart. or fractions from an extract of *Combretum laurifolium* Mart., alone or in combination, may be incorporated into a solution, cream, or gel using a pharmaceutically acceptable vehicle for topical application, or transdermal application.

Although the foregoing specific details describe certain embodiments of this invention, persons reasonably skilled in the art will recognize that various changes may be made in the details of this invention without departing from the spirit and scope of the invention as defined in the appended claims and considering the doctrine of equivalents. Therefore, it should be understood that this invention is not to be limited to the specific details shown and described herein.

What is claimed is:

1. A method of treating inflammation in a patient in need thereof, comprising:
   administering a therapeutically effective amount of a *Combretum laurifolium* Mart. extract to said patient.

2. The method of claim 1, wherein said extract is a methanol extract of *Combretum laurifolium* Mart.

3. The method of claim 1, wherein said extract is an aqueous extract of *Combretum laurifolium* Mart.

4. A method of treating breast cancer in a patient in need thereof, comprising:
   administering a therapeutically effective amount of a methanol extract of *Combretum laurifolium* Mart. to said patient.

5. The method of claim 4, wherein said therapeutically effective amount of said extract of *Combretum laurifolium* Mart. is administered parenterally in a pharmaceutically acceptable vehicle.

* * * * *